United States Patent [19]
Fischer et al.

[11] Patent Number: 5,646,046
[45] Date of Patent: Jul. 8, 1997

[54] METHOD AND INSTRUMENT FOR AUTOMATICALLY PERFORMING ANALYSIS RELATING TO THROMBOSIS AND HEMOSTASIS

[75] Inventors: Timothy J. Fischer, Raleigh; Janet B. Callahan, Chapel Hill; Paul Joseph Braun, Durham; Thomas Beecher Givens, Rougemont, all of N.C.; Julie F. Hoffman, Ypsilanti, Mich.; William Chester Hulette, Hillsborough, N.C.; John Glenn Link, Durham, N.C.; Charles Hermas Swope, Raleigh, N.C.

[73] Assignee: AKZO Nobel N.V., Arnhem, Netherlands

[21] Appl. No.: 389,986

[22] Filed: Feb. 14, 1995

Related U.S. Application Data

[63] Continuation of Ser. No. 107,381, Aug. 16, 1993, abandoned, which is a continuation-in-part of Ser. No. 833,950, Feb. 11, 1992, Pat. No. 5,236,666, which is a continuation-in-part of Ser. No. 443,951, Dec. 1, 1989, abandoned.

[51] Int. Cl.$^6$ .................................................. G01N 35/02
[52] U.S. Cl. .................. 436/49; 436/43; 436/47; 436/48; 436/50; 436/55; 422/63; 422/65; 422/67; 422/73
[58] Field of Search .................. 422/63–67, 68.1, 422/73, 82.05, 105; 436/43, 47–50, 54, 55, 174, 180, 164, 807; 364/497

[56] References Cited

U.S. PATENT DOCUMENTS

| | | |
|---|---|---|
| D. 266,589 | 10/1982 | Gilford et al. |
| D. 283,845 | 5/1986 | Lief et al. |
| D. 303,837 | 10/1989 | Albert. |
| D. 325,090 | 3/1992 | Karp et al. |
| 3,774,237 | 11/1973 | Hardaway, Jr. |
| 3,912,535 | 10/1975 | Rauser. |
| 3,960,020 | 6/1976 | Gordon et al. |
| 3,967,168 | 6/1976 | Christensen. |
| 4,067,653 | 1/1978 | Fletcher et al. |

(List continued on next page.)

FOREIGN PATENT DOCUMENTS

| | | |
|---|---|---|
| 159289 | 12/1979 | Japan. |
| 0188849 | 9/1985 | Japan. |
| 0240861 | 9/1989 | Japan. |

OTHER PUBLICATIONS

McCoy et al., "Quality Control in Flow Cytometry for Diagnostic Pathology," *A.J.C.P.*, vol. 93, No. 4 (Supp. 1) Apr. 1990, pp. S27–S37.

A. Girolami et al., "Study of a new Chromogenic Substrate for the Prothrombin Time Determination," *Folia Haemotol.*, vol. 114, No. 6, pp. 881–895, Abstract No. 06581271, 1987.

Alperts, Nelson L., *Clinical Instruments Systems*, vol. 9, No. 5, pp 1–7 (1988).

*Primary Examiner*—Long V. Le
*Attorney, Agent, or Firm*—Gregory R. Muir; William M. Blackstone

[57] ABSTRACT

This invention relates to a novel, fully automated spectrophotometric analyzer and method used for testing blood samples in the clinical laboratory for thrombosis and hemostasis properties. The analyzer tests samples in a fully randomized format, and is fully automated in the areas of specimen handling, sample preparation, optical inspection, data analysis and total quality control for imprecision and bias.

40 Claims, 10 Drawing Sheets

U.S. PATENT DOCUMENTS

| | | | |
|---|---|---|---|
| 4,076,503 | 2/1978 | Atwood et al. | |
| 4,092,632 | 5/1978 | Agulnek. | |
| 4,170,311 | 10/1979 | Spaw. | |
| 4,187,077 | 2/1980 | Covington et al. | |
| 4,204,839 | 5/1980 | Wu et al. | |
| 4,217,780 | 8/1980 | O'Connell et al. | |
| 4,227,810 | 10/1980 | Sandrock et al. | |
| 4,264,161 | 4/1981 | Hosoe et al. | |
| 4,302,965 | 12/1981 | Johnson et al. | |
| 4,305,723 | 12/1981 | Kolber et al. | |
| 4,318,885 | 3/1982 | Suzuki et al. | 422/68 |
| 4,329,149 | 5/1982 | Schoonover et al. | |
| 4,356,733 | 11/1982 | Braunweiler. | |
| 4,366,241 | 12/1982 | Tom et al. | 435/7 |
| 4,409,334 | 10/1983 | Lill et al. | |
| 4,434,672 | 3/1984 | Williamson et al. | |
| 4,463,615 | 8/1984 | Buzza. | |
| 4,468,124 | 8/1984 | Berick. | |
| 4,483,927 | 11/1984 | Takekawa. | |
| 4,497,774 | 2/1985 | Scordato | 422/73 |
| 4,516,437 | 5/1985 | Pedroso et al. | |
| 4,517,160 | 5/1985 | Galle et al. | 422/65 |
| 4,543,335 | 9/1985 | Sommer er al. | |
| 4,574,850 | 3/1986 | Davis. | |
| 4,625,096 | 11/1986 | Fletcher. | |
| 4,636,477 | 1/1987 | Ronka et al. | |
| 4,647,431 | 3/1987 | Sekine et al. | |
| 4,665,553 | 5/1987 | Gershman et al. | |
| 4,685,801 | 8/1987 | Minekane. | |
| 4,685,880 | 8/1987 | Meguro et al. | |
| 4,695,430 | 9/1987 | Coville et al. | 422/65 |
| 4,708,886 | 11/1987 | Nelson. | |
| 4,718,762 | 1/1988 | Wiget et al. | |
| 4,727,032 | 2/1988 | Baisch et al. | |
| 4,727,033 | 2/1988 | Hijikata et al. | |
| 4,731,225 | 3/1988 | Wakatake. | |
| 4,736,638 | 4/1988 | Okawa et al. | |
| 4,756,200 | 7/1988 | Ramsner et al. | |
| 4,766,078 | 8/1988 | Gang | 435/291 |
| 4,767,716 | 8/1988 | Sakamaki et al. | |
| 4,774,055 | 9/1988 | Wakatake. | |
| 4,785,407 | 11/1988 | Sakagami. | |
| 4,817,443 | 4/1989 | Champseix. | |
| 4,822,331 | 4/1989 | Taylor. | |
| 4,829,837 | 5/1989 | Tefler. | |
| 4,834,944 | 5/1989 | Wakatake. | |
| 4,844,868 | 7/1989 | Rokugawa. | |
| 4,849,340 | 7/1989 | Oberhardt. | |
| 4,861,554 | 8/1989 | Sakuma. | |
| 4,863,690 | 9/1989 | Berthold et al. | |
| 4,865,986 | 9/1989 | Coy et al. | |
| 4,919,887 | 4/1990 | Wakatake. | |
| 4,921,097 | 5/1990 | Finke et al. | |
| 4,933,146 | 6/1990 | Meyer et al. | |
| 4,958,295 | 9/1990 | Davidson et al. | 364/497 |
| 4,959,199 | 9/1990 | Brewer. | |
| 4,971,913 | 11/1990 | Manabe et al. | 436/55 |
| 4,985,207 | 1/1991 | Hayashi. | |
| 4,989,623 | 2/1991 | Hoffman et al. | |
| 5,002,392 | 3/1991 | Swope et al. | 356/328 |
| 5,027,075 | 6/1991 | Harding, Jr. | |
| 5,030,418 | 7/1991 | Miyata. | |
| 5,038,852 | 8/1991 | Johnson et al. | |
| 5,040,162 | 8/1991 | De Rozarieux et al. | |
| 5,040,894 | 8/1991 | Karp et al. | |
| 5,049,826 | 9/1991 | Sasao. | |
| 5,055,262 | 10/1991 | Sakagami. | |
| 5,066,336 | 11/1991 | Hoffman et al. | |
| 5,068,181 | 11/1991 | Driscoll et al. | |
| 5,084,251 | 1/1992 | Thomas. | |
| 5,100,622 | 3/1992 | Mimura et al. | 422/67 |
| 5,245,176 | 9/1993 | Haugen et al. | |

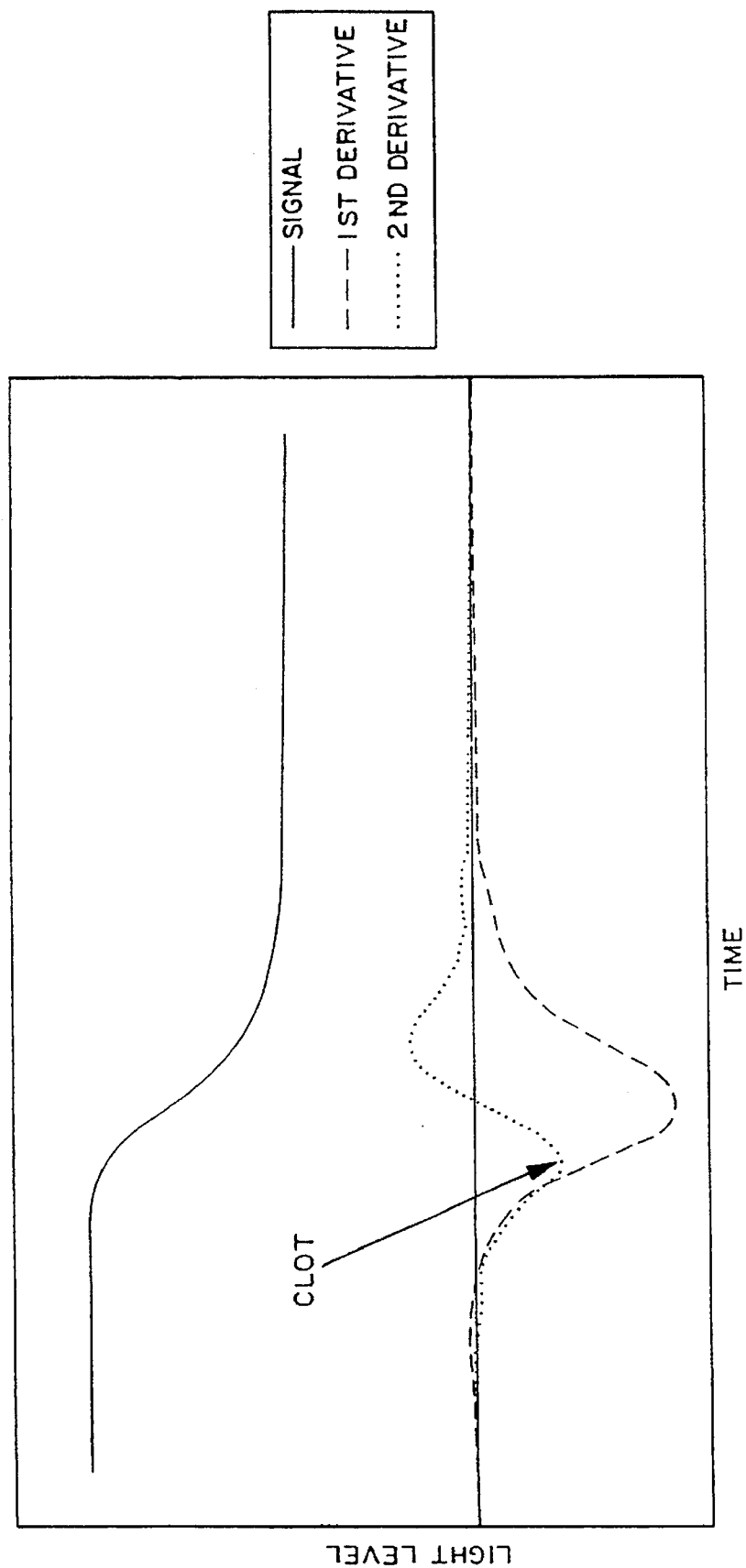

METHOD AND INSTRUMENT FOR AUTOMATICALLY PERFORMING ANALYSIS RELATING TO THROMBOSIS AND HEMOSTASIS

This is a continuation of U.S. Ser. No. 08/107,381, filed Aug. 16, 1993, now abandoned, which is a continuation-in-part of U.S. Ser. No. 07/833,950, filed Feb. 11, 1992 now U.S. Pat. No. 5,236,666 which is a continuation-in-part of U.S. Ser. No. 07/443,951, filed Dec. 1, 1989, now abandoned.

This application is additionally related to the following copending U.S. Patent Applications and issued patents, which are owned by the Assignee of the present Application, and the disclosures of all but No. 6 are incorporated herein by reference:

(1) Ser. No. 07/443,952, to Swope et al., titled "Multichannel Optical Monitoring Systems", now U.S. Pat. No. 5,002,392;

(2) Ser. No. 07/443,956, to Karp et al., titled "Cuvette and Linear Drive Mechanism Therefor", now U.S. Pat. No. 5,040,894; and (3) Ser. No. 07/443,954, to Hoffman et al., titled "Apparatus and Method for Cleaning Reagent Delivery Probes", now U.S. Pat. No. 4,989,623.

(4) Ser. No. 07/443,784, to Karp et al., titled, "Cuvette", now U.S. Patent Des. 325,090.

(5) Ser. No. 07/674,957, to Keiter et al., titled, "Heated Liquid Sampling Probe for an Automated Sampling Apparatus," now U.S. Pat. No. 5,178,019.

(6) Ser. No. 07/916,712, to Lewis et al., titled, "Cassette and Cuvette Loading Mechanism", now U.S. Pat. No. 5,364,592.

(7) Ser. No. 07/896,579, to Haugen, titled, "Method for Scanning Photodiodes", now U.S. Pat. No. 5,245,176.

(8) Ser. No. 07/443,953, to Driscoll, titled, "Method of Monitoring Reagent Delivery in a Scanning Spectrophotometer," now U.S. Pat. No. 5,068,181.

This invention relates to a novel, fully automated spectrophotometric analyzer and the method used for assaying for thrombosis and hemostasis properties of blood samples. The analyzer tests samples in a fully randomized format, and is fully automated in the areas of specimen handling, sample preparation, optical inspection, signal processing and quality assurance/control for imprecision and bias allowing for numerous assays to be performed on a single sample. The assays vary considerably in nature and fall into three categories: clot based, chromogenic, and immunological. No single automated methodology or instrumentation currently exists that successfully performs all of these types of assays concurrently.

BACKGROUND OF THE INVENTION

Thrombosis and hemostasis testing is the in vitro study of the ability of the blood to form clots and to break clots in vivo. As thrombotic and hemostasis pathways form a part of very important disease states ranging from hemophilia to strokes and heart attacks, the testing of a patients capabilities in thrombosis and hemostasis is a critical diagnostic tool. Should a patients ability to form clots in vitro fall outside of the established norm, or should certain markers be out of the normal range, the serum or plasma sample is further assayed to determine the reason for the problem. These assays are in standard use in all hospital laboratories.

Coagulation assays began, and are still done in many instances, in a test tube using hand methods. Early on, the goal was to determine if a patients blood sample would clot after certain materials were added. It was later determined that the amount of time it took for the sample to clot was related to congenital or acquired disorders. This type of testing is extremely dependent on the laboratory technologist, and so, some form of standardization was seen to be needed. As technology improved and stronger correlations between in vivo conditions and in vitro assays were established, semi-automatic coagulation analyzers began to appear.

These coagulation analyzers primary usefulness is to remove the subjectiveness in determining the exact second a clot forms in a sample in vitro. However, these analyzers did and do not have the automation required to remove variability associated with sample preparation. Furthermore, advances in clinical thrombosis and hemostasis assays resulted in the development of new types of assays that aided in the diagnosis and treatment of a patient and semi-automated coagulation analyzers seldom possess the ability to perform more than one assay at a time. This is because reagent pathways are dedicated to a single reagent, resulting in a limited number of assays that can be performed on each instrument. Generally, the semi-automated instrumentation performs one test in a batch mode, maintaining one profile of temperature vs. time for each different type of assay.

Semi-automated analyzers also require the technician to manually deliver the plasma sample. A new sampling device, generally a pipette tip, is used for each specimen to eliminate plasma cross-contamination between samples. Using a common sampling means for reagents and samples requires novel approaches to eliminate cross contamination of samples and reagents.

In order to have the next generation of analyzers, fully automated analyzers must be developed to be able to use the same sampling device for all specimens and to have common pathways for delivery of multiple reagents, and to provide a universal time and temperature profile compatible with a multitude of assays.

Additionally, any complex computations needed to be performed for an assay are done by an operator when semi-automated analyzers are used. Differences in operators techniques in analyzing data lead to increased levels of inaccuracy of the data. Another feature needed to improve coagulation testing is improved and standardized data analysis techniques to obtain the desired performance characteristics from inter and intra laboratory comparisons, which would result in a higher standard of care for the patient.

Quality control and system monitoring of the semi-automated coagulation analyzers are primitive and inadequate when compared to the state of the art.

The next generation of analyzers, a fully automated thrombosis and hemostasis analyzer, requires a statistically controlled, on-line quality assurance program that monitors the system integrity, as the analysis are being performed. This program must not only identify failures after they have occurred, but predict potential failures before they occur.

Another area of the clinical laboratory, the clinical chemistry laboratory, has had fully automated analyzers for a number of years. The tests performed and the types of reactions read, including colorimetric, fluorescent and luminescent measurement, are substantially different and have endpoints that are easier to detect than do coagulation-based tests, those performed in the coagulation laboratory. The same progress towards full automation has not been seen in the coagulation laboratory as in the clinical chemistry laboratory.

In general, the basic tests or assays performed in the coagulation laboratory using plasma, serum or whole blood include performing the Partial Thromboplastin Time ("PTT"), the Prothrombin Time ("PT"), the Activated Partial Thromboplastin Time ("APTT"), testing for deficiencies in Factors such as Factors II, V, VII, VIII, IX, XI, XII and others, and chromogenic and immunological testing for thrombosis or hemostasis markers. These, among others, have proven to be much more difficult to do on automated equipment than have the clinical chemistry tests. This is because the tests run in the coagulation laboratory usually: (1) involve unique time/temperature profiles; (2) are extremely sensitive to both reagent and plasma carryover; (3) require unique data analysis; and (4) have unique quality control requirements.

A method for automatically performing a variety of coagulation-related assays and a fully automated coagulation analyzer is needed to perform a host of assays in a totally random format that would expedite patient diagnosis. It must have the ability to control the sample preparation stages of an in vitro assay; to perform all thrombosis and hemostasis assays using a common temperature profile; to measure the reaction that occurs when the appropriate materials are added; and to determine both the immediate response as well as to provide mathematical tools for calculating complex results. This entire process should be monitored using an on-line quality control package that is designed to minimize imprecision associated with random error and to minimize bias associated with error due to the system itself, systemic error.

This type of fully automated coagulation analyzer would provide more accurate results that in turn would allow for quicker and more accurate diagnosis of current or predicted illness, thereby allowing for better treatment of the patient.

SUMMARY OF THE INVENTION

The present invention includes a method for automatically assaying for hemostasis and thrombosis parameters in a plasma, serum or whole blood sample comprising:

a) providing a programming input means for identifying the sample and scheduling one or more hemostasis and thrombosis-related assays to be performed on the sample;

b) providing a specimen handling means for automatically transferring an aliquot of the sample from a holding device to a test well in a cuvette;

c) providing a sample preparation means for automatically adding reagents needed for an assay to measure hemostasis or thrombosis parameters to the sample in the test well at a specified time and temperature, accommodating a universal thermal profile, to obtain a reaction, wherein the order of the reagents added can be in a random access format thereby eliminating the need for batch analysis;

d) providing a detecting means for detecting the reaction in the well and measuring the data from the reaction;

e) providing a processing means for mathematically processing the measured data to evaluate a change in or magnitude of the measured data from the reaction in the well;

f) providing a reporting means to report said results of the evaluation by the processing means; and g) simultaneously with all of steps a)–f) above, providing a quality assurance means for monitoring the performance of the method and evaluating the validity of the reported data for the sample, thereby automatically performing hemostasis and thrombosis-related assays and determining and reporting results on hemostasis and thrombosis parameters in the sample.

The present invention also provides a fully automated coagulation analyzer that responds to all of the needs stated above. The linear, spectrophotometric analyzer performs multiple hemostasis and thrombosis assays on samples of serum, plasma or whole blood in a totally random order. It is fully automated in terms of specimen handling, sample preparation, optical inspection, signal processing, and total quality control for imprecision and bias. All hemostasis and thrombosis assays performed on the analyzer have been designed to share a common temperature profile, thereby allowing the random performance of assays. Each of these functions are also internally controlled through quality assurance programming. Each assay is defined by an assay definition file ("adf") allowing for flexibility in method definition. This flexibility is required in order to obtain the unique performance characteristics for each assay. Improvements in linearity, accuracy and the minimization of bias can be achieved by optimization of adf parameters.

BRIEF DESCRIPTION OF THE DRAWINGS

FIG. 11 shows a smoothed signal, smoothed first derivative of that signal, and smoothed second derivative for data collected from a normal APTT assay. The location of the maximum of the second derivative (the clot time), is identified.

DETAILED DESCRIPTION OF THE INVENTION

Figure 1:
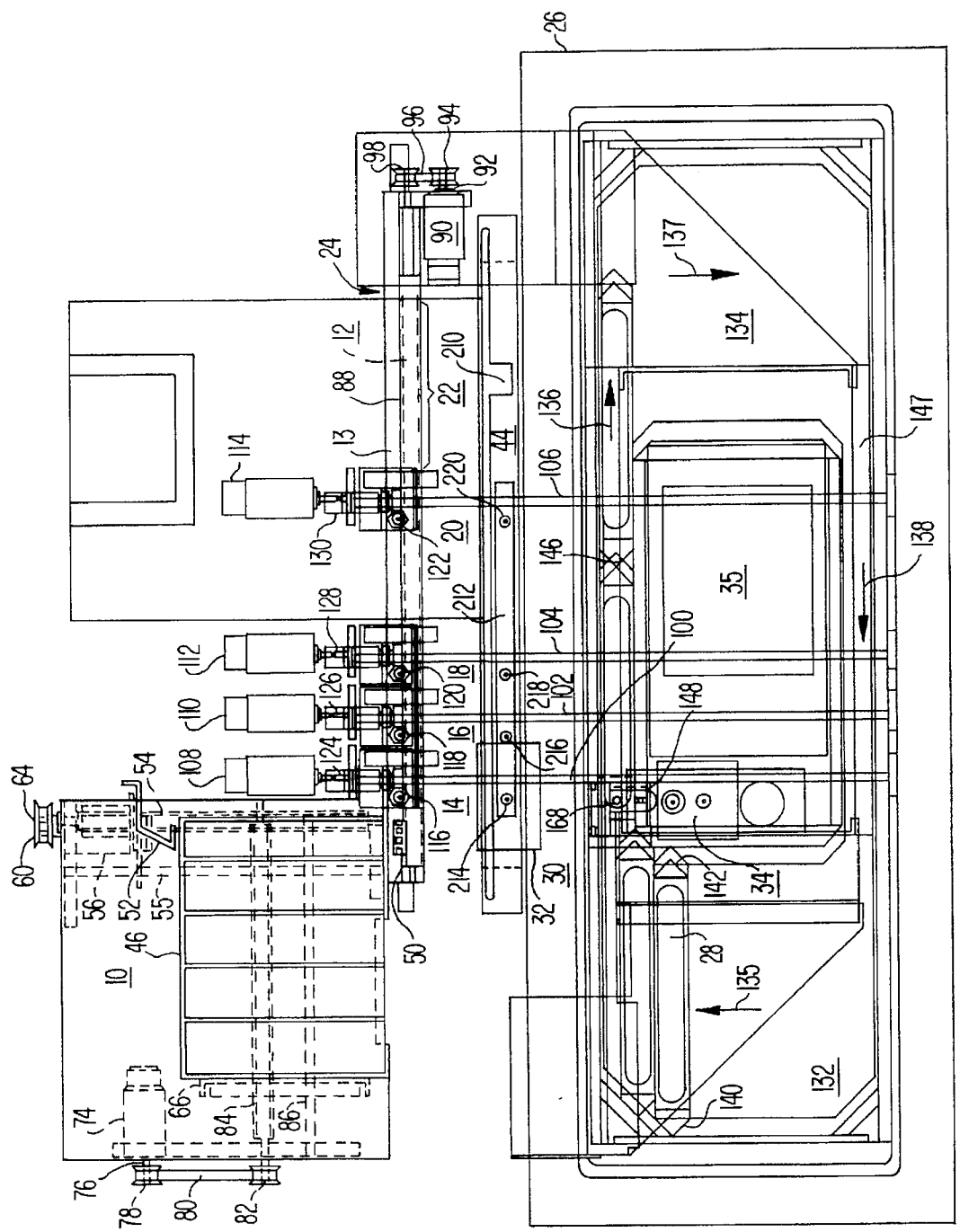
FIG. 1 is a schematic top elevation of a sample handling system in a optical evaluation instrument according to the invention.

The needs of the clinical coagulation laboratory for a fully automated coagulation analyzer have been met with this invention. Provided is an optical evaluation instrument and method that can handle a high throughput of patient samples with a high degree of versatility, adaptability and reliable automation. This is walkaway automation once patient samples still sealed in the original evacuated collection tube are loaded into the system.

The present invention includes a method for automatically assaying for hemostasis and thrombosis parameters as described above, in a plasma, serum or whole blood sample in a holding device, such as an evacuated collection tube, that can be stoppered. The assays may be performed in either a batch or random fashion, wherein the same assay or test is performed on all samples, multiple different assays are performed on each sample and a different assay is performed on each sample. This is accomplished by providing an integrated programming input means for identifying the sample and scheduling one or more hemostasis and thrombosis-related assays to be performed on the sample in any order. The programming means will accept and will allow the assays to be performed in a random format, i.e. in any order.

Next in the method is providing a specimen handling means for automatically transferring an aliquot of the sample from a holding device or a collection tube, with or without a stopper, to a test well in a cuvette. Because of various issues regarding the exposure of laboratory workers to blood borne contagious disease, being able to provide a specimen handling means to pierce the septum or stopper without a human present is a definite asset in a clinical instrument or method.

Also, in the method is providing a sample preparation means for automatically adding the reagents needed for an assay to measure hemostasis or thrombosis parameters to the sample in the test well at a specified time and temperature, accommodating a universal thermal profile, to obtain a reaction, and wherein the order of the reagents added can be in a random format eliminating the need for batch analysis. This methodology is needed because each assay or test performed in the coagulation laboratory is done with different time and temperature needs. The present method provides for a common universal thermal profile wherein each assay or test can be done within its particular parameters. The method provides for a heating and cooling track where each sample moves forward, but each at the speed needed for the assay to be performed, and the means for automatically adding the reagent needed at the proper temperature. Once the proper reagents are added at the proper time and temperature, the reaction begins.

Next, the method provides a detecting means for detecting the reaction in the well, and takes the result of said detection to mathematically compute data. This data, or the raw result of the assay or test, is provided a processing means wherein the computed data is evaluated to determine the change in or the magnitude of the reaction in the well, and when required, to transform the data into a diagnostically useful result.

Simultaneously with all of steps above, the method provides a quality assurance means for monitoring the performance of the method and evaluating the validity of the reported data for the sample, thereby automatically performing hemostasis and thrombosis-related assays and determining and reporting results on hemostasis and thrombosis parameters in the sample.

A preferred way of performing the above described method of testing a large number of samples in a random order is done with the following instrument.

Overview of the Automated Analyzer

The analyzer is fully automated in terms of specimen handling, sample preparation, optical inspection, signal processing and total quality control for imprecision and bias, and a quality assurance program.

A. The Specimen Handling Segment

The specimen handling segment of the analyzer is divided into four basic components consisting of positive patient identification of the sample, screening for preanalytical variables, the ability to do closed container sampling and the ability to continuously supply cuvette wells for sample evaluation.

In greater detail, the specimen handling segment consists of:

1) a means for storing and continuously supplying a plurality of cuvettes to be used in the assays, each cuvette containing a plurality of reaction wells;

2) the optically readable code, such as a bar code or other coding, present on or incorporated into the sample collection tube or holding device containing a sample of serum, plasma or whole blood, is a patient identification and tracking device, and is also used in assay entry and automatic tracking of the assay during sample evaluation;

3) a means for the screening of and evaluating preanalytical variables prior to the beginning of any assay, such as hemolysis, bilirubin and lipemia; and 4) a sample insertion station including a means for automatically aspirating sample from the sample collection tube or holding device with or without a stopper and for automatically dispensing the aspirated sample into a reaction well of a cuvette.

B. The Sample Preparation Segment

The sample preparation segment of the analyzer consists of four components: the means for defining unique reagent transferring sequences for each assay, random access ability, or the ability for a probe to aspirate reagent from a reagent container and dispense it into a predetermined cuvette well in any order and to aspirate and deliver different plasmas without cross contamination; the universal profile testing method; a means for performing auto dilutions of the sample; and a means for monitoring reagents and samples.

In greater detail, the sample preparation segment consists of:

1) an assay definition file ("adf") that allows for flexibility in how the reagents and plasmas are delivered. This flexibility is defined in terms of aspiration and dispense velocities, temperature, time out (delay) or timing sequences;

2) a reagent station, including a sample preparation means having the ability to randomly aspirate selected amounts of selected reagents from selected reagent containers as needed, and for dispensing the aspirated reagents into a reaction well of a cuvette according to the directions given in a programmed test for the sample in that reaction well. Each well of the cuvette may be programmed to have a different assay performed, and the reagent and sample in the reaction well forms a reaction volume which exhibits optical characteristics to be monitored by the analyzer;

3) a means for providing a universal temperature profile for the different assays programmed on the analyzer, which is an arrangement for temperature regulation of a fluid sample in a cuvette transported through various stations of the automated system for optically monitoring the sample in the cuvette, comprising: a means for transporting the cuvette through the various stations of the sample and reagent delivery system and optical monitoring system, the sample temperature being controlled by the system; cooling means for cooling the sample in the first portion of the profile; heating means for heating the sample in the third portion of the profile in such a way as to maintain the sample temperature within base tolerance constraints; and a second section providing a means of providing a temperature ramp that defines the sample transition from the initial cool temperature to final warm temperature;

4) a means for automatically diluting samples, reference materials, and control materials through the use of programmed probes that perform a wide range of serial and nonserial dilutions; and 5) a temperature controlled housing for storing a plurality of reagent containers, each containing a respective reagent, and a plurality of sample collection tubes, each containing a fluid sample and presenting an optically readable code, such as a bar code or other equivalent coding, identifying the sample and a test to be performed on the sample. There is also a reagent tracking system that monitors the amount of available fluid in each discrete vial or container of reagent, present as a means for sensing liquid levels, one embodiment being a liquid-level sensor on each probe that aspirates and dispenses liquid.

C. The Optical Inspection Segment

The optical inspection segment of the automated analyzer consists of three components, 1) a means for multiple wavelength analysis; 2) the use of a broad spectrum of wavelengths; and 3) continuous normalization of the fluctuations in light levels associated with sample to sample variability.

The optical inspection portion of the analyzer is provided for by:

1) and 2) a multichannel optical monitoring system as described in commonly owned U.S. Pat. No. 5,002,392, issued on Mar. 26, 1991, and incorporated herein by reference and commonly owned U.S. patent application Ser. No. 07/896,579, "Method for Scanning Photodiodes", also incorporated herein by reference; and 3) fluctuations in light levels associated with sample to sample variability, such as differences in color from sample to sample, are normalized through a quality assurance program prior to data analysis of the test results.

D. The Signal Processing Segment

The signal processing segment of the analyzer consists of three components: the determination of kinetic endpoints; complex processing that determines endpoints other than clot formation, such as immunological complexes or chromogenic endpoints; and an on-line database against which each test result can be compared.

In greater detail, the signal processing segment of the analyzer consists of:

1) a means for determining kinetic endpoints, for example, a computer program, that is able to determine the rate of acceleration that a clot is forming. This analysis is unique in that it is based on the kinetics of clot formation as opposed to the use of a threshold, which is sensitive to biological, mechanical and electrical artifacts, thereby giving more accurate test results.

2) a means for determining the endpoint of a variety of assays other than those based on clot formation. For example, chromogenic assays such as ATIII and Protein C, and immunologic assays based on the interactions of antigens and antibodies, such as the assay for D-dimer, are read based on color changes or the presence or absence of agglutination or some type of label; and 3) a means for creating and storing reference curves that can be used for the evaluation of controls and patient samples.

Each of the above segments of the coagulation analyzer is integrated with on-line quality control and quality assurance programming. These are conducted to minimize bias and imprecision throughout the analyzer.

E. The Quality Assurance Segment

The satisfactory performance of any and all clinical laboratory assays depends on an effective quality control or quality assurance program, which controls each of the parameters listed below. Control of these parameters minimizes imprecision associated with random error and minimizes bias associated with systemic error. The parameters controlled by the analyzer are:

A) specimen integrity and handling;
B) reagent and expendable availability and quality;
C) suitability and sensitivity of mechanical metering devices;
D) suitability and sensitivity of reaction inspection and measuring devices;
E) suitability and sensitivity of data analysis methods, wherein statistical quality control rule analysis of the control data allows for the monitoring of the system in statistical control, assuring the validity of the results; and
F) minimized bias when compared to reference methods.

In order to assure accurate laboratory assay results, it has always been necessary to devise quality assurance methods to monitor important variables of each of the above critical parameters. This type of monitoring is equally necessary for manual, semi-automated and automated analytical methods. Prior to the present invention, skilled laboratory workers were responsible for monitoring these important variables for manual and semi-automated analytical methods using rudimentary off-line means. Some of these means included a traditional Levy Jennings approach to control ruling, visual inspection of samples for anomalies and no real-time monitoring of some instrument parameters was available. But the present invention requires on-line monitoring using sophisticated computer programming and integrated means.

Although each type of coagulation laboratory assay has specific critical parameters within the general parameters described above, some additional hemostasis and thrombosis assay critical parameters include:

1) Positive patient identification which includes bar code or similar identifier tracking, Delta check with previous specimen from the same patient; physiologic panic value evaluation; operational comments regarding the sample that follow data to the final report; and a statistical evaluation of replicate tests.

2) Preanalytical Variables are variables that can contribute to an anomalous result. Examples are specimen age, plasma with clot contamination, the amount of anticoagulant present in the blood collection tube to plasma collected ratio, nonanalyte interferences, optimized thermal storage of specimens to offset degradation with activation, hemolysis of sample, bilirubin content, and lipemic samples.

3) Sampling from a primary specimen container that allows for repeated testing from the same closed container without plasma carryover effects or aerosolization of the blood samples.

4) Reagent and Expendable Availability—a broad diagnostic assay menu supported with the proper reagents, which are monitored, tracked and flagged for the operator when the levels are low; a liquid level sensor on the probe via, for example, capacitance touch facilities; flagging failure of the analyzer to dispense; logic programming omitting the performance of an assay if sufficient reagents not available; bar code or similar identifier identification of the actual placement of a reagent in reagent tray; and preloaded cuvette cassettes handling a large number of cuvettes insure the optical clarity of the cuvette by minimizing handling of cuvettes.

5) Reagent quality is insured by refrigerated storage; by a reagent tray cover that minimizes evaporation and condensation; by the tracking of expiration dates; by tracking of reagent quality within each run, day-to-day, and month-to-month via an on-board quality control program using controls; by an assay specific quality control program which employs statistical rules with the ability to detect errors in the reagents; by tracking reagent quality independently of biological control plasmas using averaged patient data parameters; by normalizing minor drifts in reagent viability over time by assay calibration using calibrator plasmas; and by stirring reagents requiring stirring to maintain homogeneous suspension.

As can be seen from the above descriptions of the various segments of the automated coagulation analyzer, the segments are interdependent. Each of the four segments, specimen handling, sample preparation, optical inspection and signal processing are monitored and regulated and checked by on-board quality assurance and quality control program, providing an oversight function for all critical parameters. Each of these segments will be now more fully discussed along with the integration of these segments with the quality control and quality assurance features of the automated coagulation analyzer.

Referring to FIG. 1, there is shown an optical evaluation instrument incorporating a sample handling system according to the invention. The principal elements of the sample handling system include a cuvette storage and loading mechanism 10, for supplying cuvettes individually to a cuvette transport mechanism 12, which advances the cuvettes along a linear track 13 through a sample insertion station 14, a plurality of reagent insertion stations 16, 18 and 20, an optical monitoring station 22 and finally, to a cuvette disposal station 24. The sample handling system additionally includes a refrigerated housing 26, for storing a plurality of evacuated collection tubes (not shown), which are transported via shuttles 28 through a programming station 30, including a bar code reader 32, for reading a preprinted bar code printed on the side of each evacuated collection tube identifying the test sample and the test to be performed, and onto sample insertion station 14, which includes a piercer 34, for piercing the septum of an evacuated collection tube for allowing a sample probe 36 (see FIG. 2) to be lowered into the sample collection tube for aspirating a fluid sample which is to be ejected into a reaction well of a cuvette located at sample insertion station 14, as described in greater detail herein below. Refrigerated housing 26, additionally encloses a reagent chamber 35, which stores a plurality of reagent containers (see FIGS. 5 and 6), which can be accessed by reagent probes 38, 40 and 42 (see FIG. 2), for aspirating selective reagents and injecting them into reaction wells located at the respective reagent insertion stations 16, 18 and 20. As used herein, reagents include any reagent, diluent, buffer, or activator which is required for any given biochemical test being performed on the patient sample according to a preprogrammed test protocol. A probe washing station 44, is provided for washing the sample and reagent probes after each dispensing action.

Figure 4:
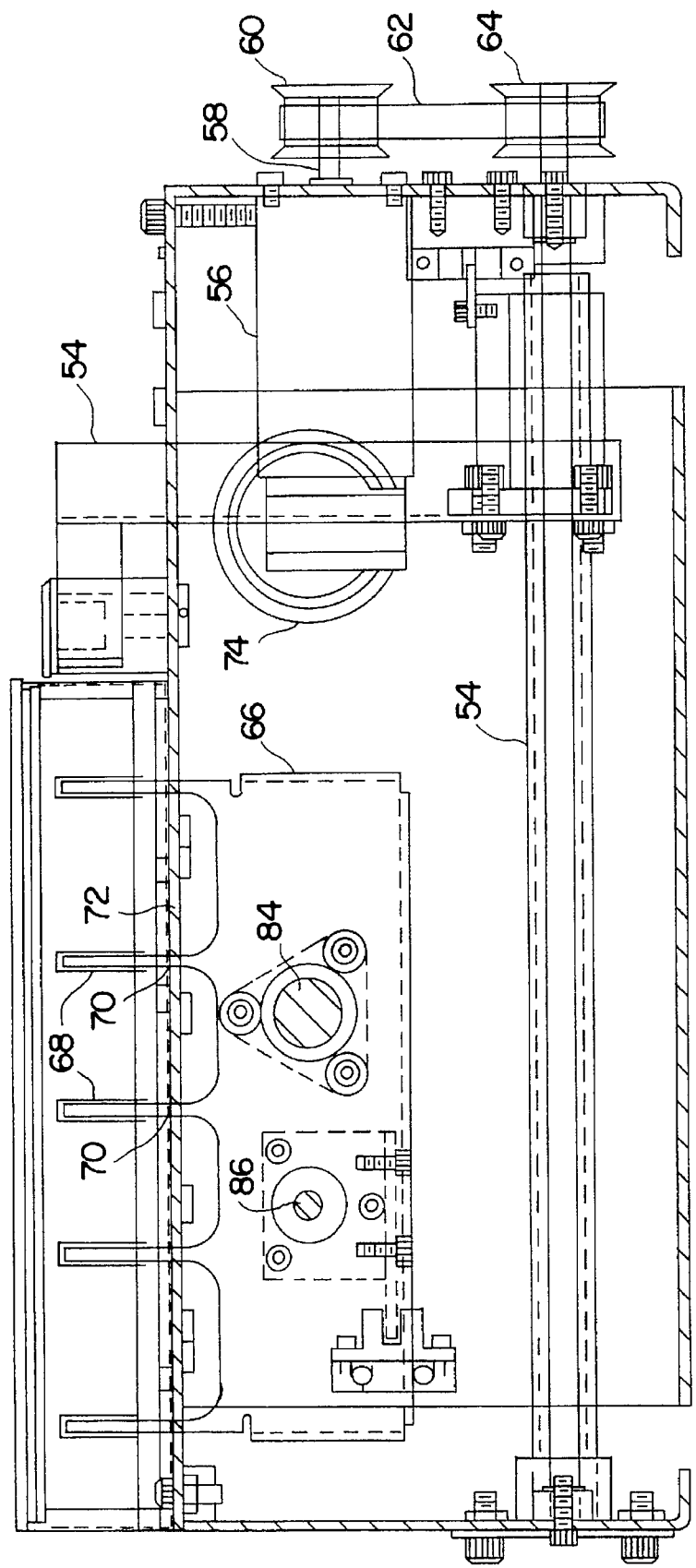
FIG. 4 is a schematic right-side elevation of the cuvette storage device of FIG. 1.

Referring to FIGS. 1 and 4, cuvette storage device 10 includes a cassette frame 46, for receiving a cassette of cuvettes arranged in the cassette in columns parallel to the right and left hand sides of frame 46 in FIG. 1. The cassettes are preferably of the type described in U.S. Pat. No. 5,040,894 to Karp et al. cited above. A plan view of one such cuvette 50 is seen in a loading position with respect to cuvette transport mechanism 12. A pusher arm 52, driven by a lead screw 54, loads cuvettes onto cuvette transport mechanism 12. A motor 56, whose shaft 58, is connected with a pulley 60 rotates a driving belt 62 which turns a pulley 64 for driving lead screw 54. A fixed guide rod 55 is provided in the usual manner for providing guidance and additional support for pusher arm 52. After a column of cuvettes is completely loaded onto cuvette transport mechanism 12, pusher arm 52 is retracted and a new column of cuvettes is moved rightwardly (in FIG. 1) by way of a cassette column drive mechanism to be in line with pusher arm 52. The cassette column drive mechanism includes a plate 66, provided with fingers 68, extending through slots 70 in a bottom support 72 of cassette frame 46. A rectangular plate (now shown), is positioned between fingers 68 and the left-hand most column of cassettes (not shown) in frame 46 for pushing the cassette columns in a rightward direction in FIG. 1. Plate 66 is driven by way of a motor 74 whose shaft 76 is connected to a pulley 78 which turns a driving belt 80 connected to a further pulley 82 which turns a lead screw 84, whose threads engage with plate 66. A fixed guide rod 86, is provided parallel to lead screw 84, for guiding plate 66 in the usual manner.

Cuvette transport mechanism 12, includes a lead screw 88, which is driven by way of a motor 90 whose shaft 92 is connected to a pulley 94 for turning a belt 96 which is connected for driving a pulley 98 connected to lead screw 88. The cuvettes are each provided with an engaging means, such as a rib having the same pitched angle as the threads of lead screw 88 which engage the lead screw threads when placed in a loading position by pusher arm 52. A cuvette 50 is shown in the loading position engaging lead screw 88. Cuvettes of this type, which desirably have four reaction wells, as shown by cuvette 50, are disclosed in the aforementioned U.S. Pat. No. 5,040,894, to Karp et al. Once engaged with lead screw 88, the cuvettes are advanced in a rightward direction in FIG. 1 along linear track 13 through the various stations as described herein for injecting a sample volume and reagents to create a reaction volume to be optically monitored at the optical monitoring station.

Linear track 13 is preferably made of a single piece of aluminum having a smooth upper surface on which the cuvettes can slide without interference. Desirably, linear track 13 is temperature controlled for controlling the temperature of the contents of the cuvette reaction wells, which contents are in heat exchange relationship with the track by way of the cuvettes. For this purpose, linear track 13 is cooled on the left side of a heat flow restriction 15 shown in FIG. 2 by way of, for example a Peltier device (not shown) to maintain the temperature of the reaction well contents at about 15° C. On the right hand side of heat flow restriction 15, linear track 13 is heated by way of a heating element 17, such as a resistive heat tape, applied to the under side of the linear track for maintaining the temperature of the reaction well contents at body temperature. Preferably, heat flow restriction 15 is formed by an elongated notch in the underside of linear track 13 so as to reduce the cross section of the track in the region of the notch and thus correspondingly reduce the heat flow by an effective amount from the heated portion to the cooled portion of the track. The upper surface of the track in the region of the notch remains smooth and continuous so as not to present any interference with the cuvettes sliding thereon. Control signals for controlling motors 56, 74, and 90, for turning respective lead screws 54, 84 and 88, to accomplish the required incremental movements of pusher arm 52, plate 66, and cuvette 50, respectively, are received from a central controller (not shown) of the instrument in a manner well understood by those skilled in the art.

Sample probe 36, and reagent probes 38, 40 and 42 are controllably moved along a horizontal path by way of respective lead screws 100, 102, 104 and 106, driven by respective motor assemblies 108, 110, 112 and 114. Vertical movement for lowering and raising sample probe 36, and reagent probes 38, 40 and 42, is accomplished by way of respective vertical gear racks 116, 118, 120 and 122, driven by corresponding vertical motor and pinion assemblies 124, 126, 128, and 130, respectively. Horizontal lead screw motors 108, 110, 112 and 114, and vertical rack and pinion motors 124, 126, 128 and 130, are selectively controlled by signals received from the instrument controller (not shown) for controlling the horizontal and vertical movement of the respective probes for aspirating and dispensing sample and reagents according to the test protocol identified from the bar code of a given sample collection tube read by bar code reader 32. Sample and reagent aspiration and dispensing by probes 26, 28, 30 and 32 is accomplished by way of positive displacement pumps (not shown) connected to the respective probes in a manner understood by those skilled in the art.

Refrigerated housing 26, comprises a double walled insulated enclosure 131, and a cooling system 133, preferably of the ducted type, for circulating cooling air within housing 26 for maintaining the temperature of sample collection tubes (not shown) mounted in shuttles 28 and reagents in reagent chamber 36 at a temperature between 4° and 8° C.

Referring to the plan view shown in FIG. 1, refrigerated housing 26, has left and right chambers 132 and 134, respectively, connected by passages 146 and 147 for storing and transporting shuttles 28, which are caused to move in a clockwise direction, as shown by arrows 135 to 138. Each shuttle 28 is provided with means for carrying a plurality of evacuated sample collection tubes of the type, for example, made by Beckton Dickinson of Rutherford, N.J., and sold under the brand name Vacutainer. The configuration of shuttles 28, and the mechanism for transporting the shuttles is disclosed in detail, for example, in U.S. Patent No. 3,418,084 to Ailington.

Briefly, each shuttle 28 has complimentary camming surfaces 140 and 142 formed at the opposite ends thereof. Shuttles 28 are disposed in rows in the respective chambers 132 and 134. A drive mechanism (not shown) comprising gears which mesh with gear tracks 29 on the bottom of the shuttles 28 (FIG. 2), drive the shuttles through passages 146 and 147 in opposite directions. The shuttle drive mechanism causes a driven shuttle to push the shuttle in front of it and the camming surfaces effect a lateral displacement in the manner described by the above-referenced patent to Ailington. The shuttles are transported, one behind the other, in passages 146, so that the evacuated collection tubes are passed first through programming station 30 where bar code reader 32 reads a previously-applied bar code on the side of the evacuated collection tube to identify the sample and the test to be performed. The information read by bar code reader 32 is fed to the instrument controller (not shown) for controlling subsequent movement of the sample and reagent probes for filling a reaction well of a cuvette transported by cuvette transporting mechanism 12 through the respective sample and reagent stations.

After having its bar code read, the evacuated collection tube is moved, by way of the shuttle and shuttle drive mechanism, a precise distance to place the evacuated collection tube in line with piercer 34. The precise positioning of the shuttle is accomplished by way of an electro-optical sensing mechanism 148 (FIG. 1), which passes a sensing beam through spaced passages 150 (FIG. 2), provided in the base of shuttles 28, for sensing when the shuttle is in the appropriate position.

Figure 3:
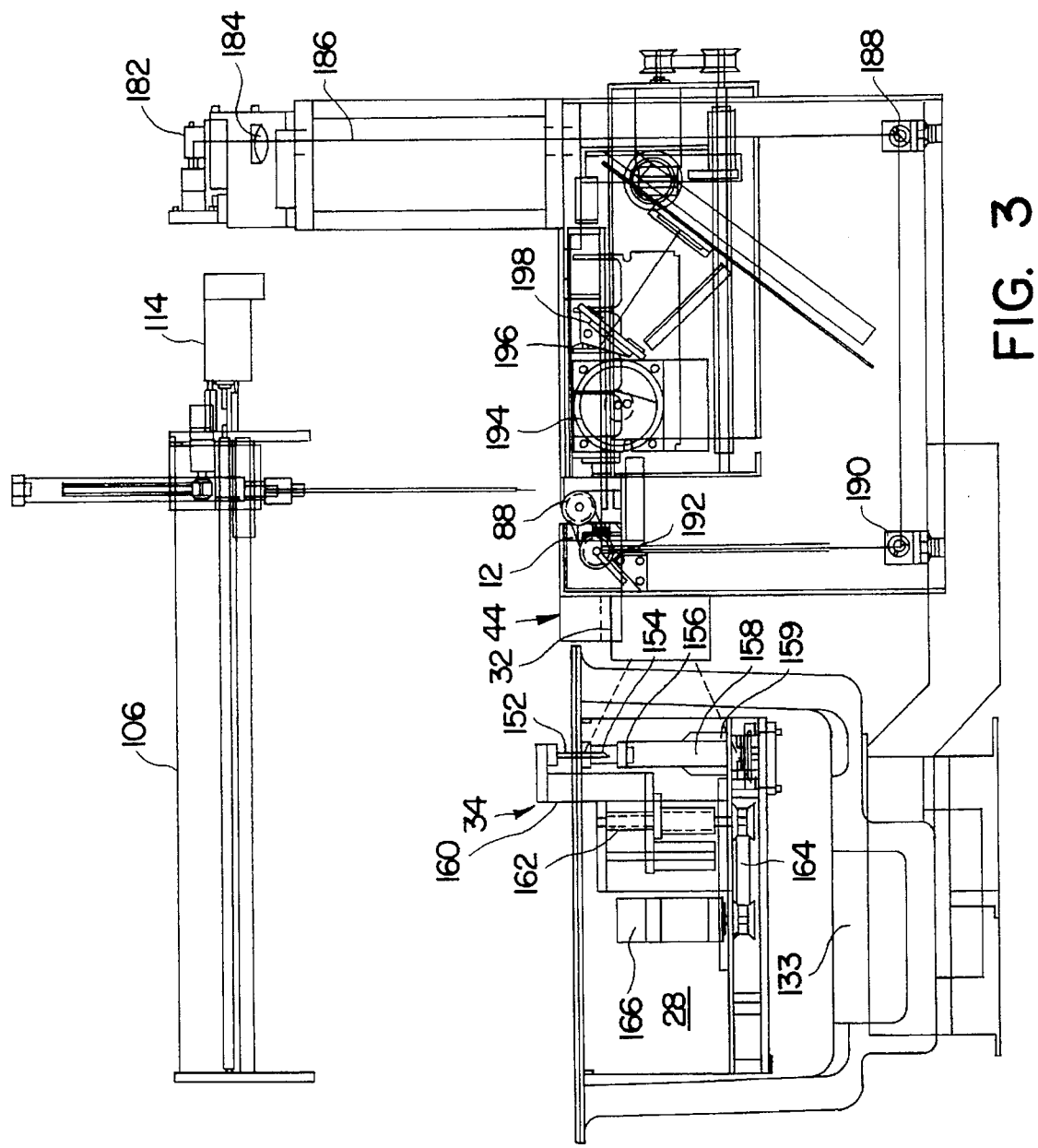
FIG. 3 is a schematic right-side elevation of FIG. 1.

Referring to FIG. 3, piercer 34 includes a piercing tube 152 having a sharp angled end 154, canted at approximately the same angle as the tip of a conventional hypodermic needle, for piercing a septum 156 of an evacuated collection tube 158. Piercing tube 152 is mounted in a support 160 which engages a vertical lead screw 162 which is connected by way of a belt and pulley system 164 to a motor 166 for driving lead screw 162. With appropriate movement of lead screw 162, piercing tube 152 is caused to be lowered for piercing septum 156 or to be removed therefrom. A holding mechanism 159 holds tube 158 in place while piercing tube 152 is inserted and withdrawn. Piercer 34 has an opening 168 (FIG. 1) at the top concentrically aligned with piercing tube 152, so that when sample probe 36 is aligned with piercing tube 152 a pathway is provided for lowering the sample probe into an evacuated collection tube 158, for aspirating a fluid sample therefrom.

Figure 5:
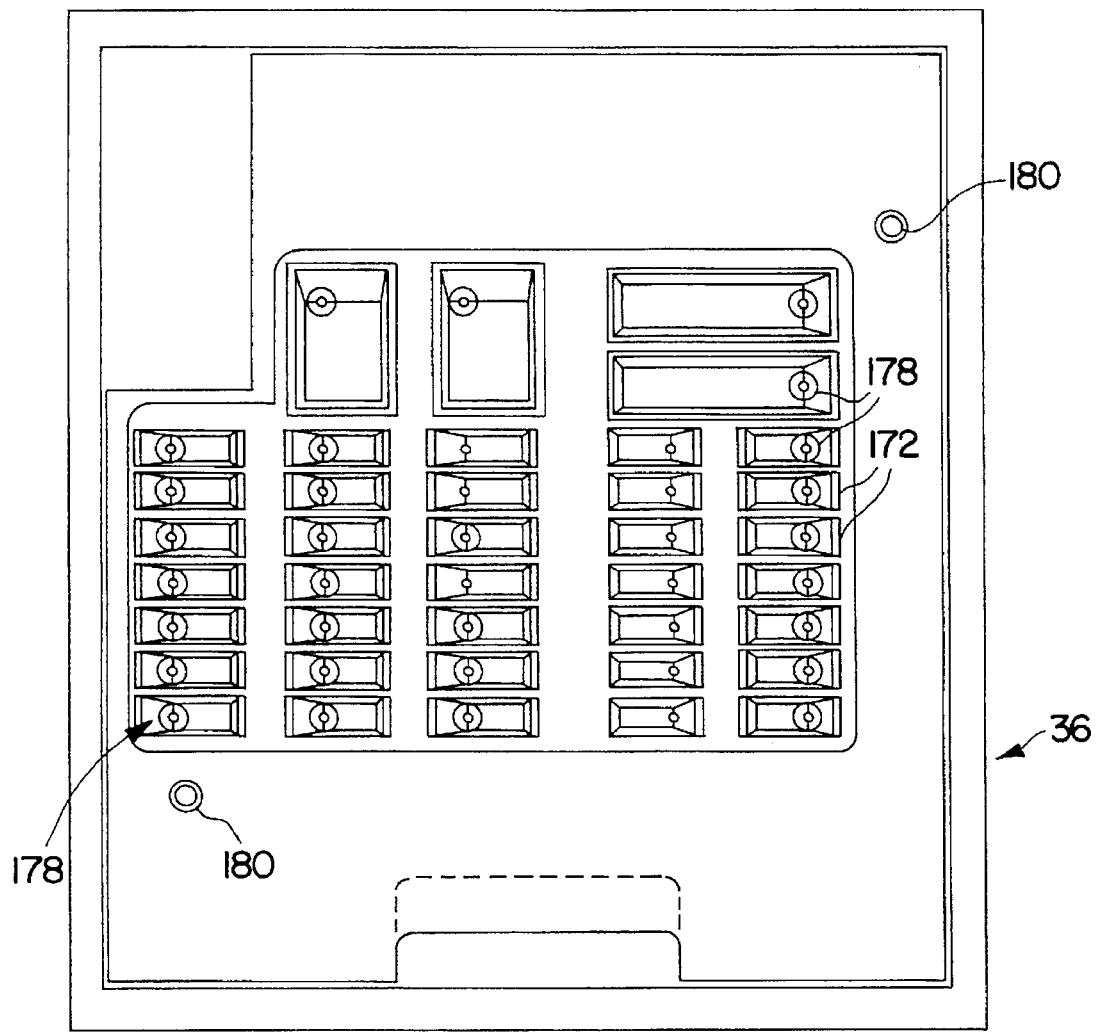
FIG. 5 is a top elevation of the reagent container block of FIG. 1.
Figure 6:
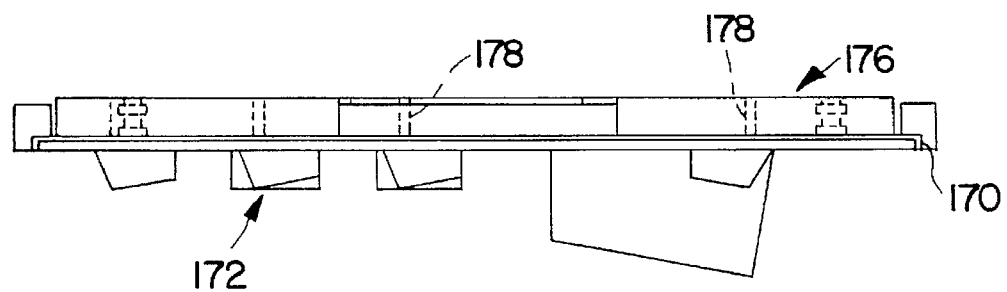
FIG. 6 is a side elevation of FIG. 5.
Figure 7:
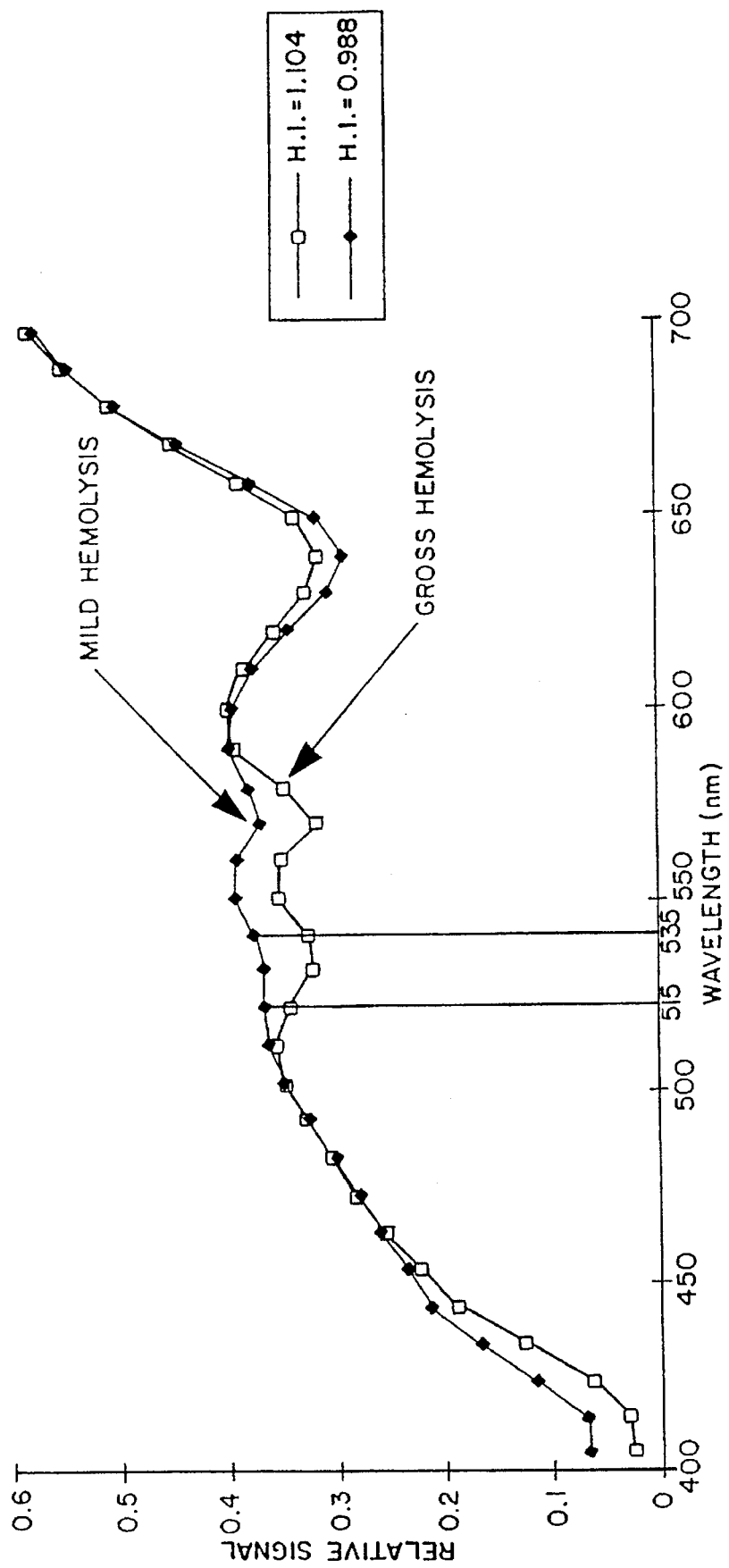
FIG. 7—The relative signal at various wavelengths is shown for two samples: a sample with mild Hemolysis, and a sample with Gross Hemolysis. Wavelengths of 515 nm and 535 nm are identified. The actual data collected is represented by data markers and these data markers are connected for each sample.

Reagent chamber 35 is shown in greater detail in FIGS. 5 and 6. As shown in these Figures, a reagent container support plate or tray 170, is provided for supporting a plurality of reagent containers or cups 172, of varying capacities. A reagent cover 176, of approximately one half inch thickness, is placed over reagent container support plate 170. Reagent cover 176 is provided with reagent probe holes 178 positioned above respective ones of reagent containers 172. Probe holes have a diameter (approximately 3 mm) slightly larger than the diameter of reagent probes 40 and 42 for permitting the probes to be lowered into selected ones of the reagent containers. Reagent cover 176 serves as an anti-evaporation cover for retarding or preventing evaporation of the reagents in reagent containers 172 while still allowing access to the reagents through probe holes 178. The anti-evaporation cover additionally serves to retard rapid temperature shifts by providing a barrier between different temperature zones. Although there are multiple holes in the anti-evaporation cover, it is of sufficient depth to provide the tortuosity necessary to retard or prevent evaporation of liquids. Desirably, reagent cover 176 is provided with locator pins 180 for accurately positioning the cover over the reagent containers and in alignment with the horizontal tracks of reagent probes 38, 40 and 42.

Probe washing station 44, comprises a trough 210, containing a cleaning solution such as bleach. An additional trough 212 is provide for receiving waste fluids and cleaning solution from the probes during the washing process. Trough 212 is provided with a plurality of riser platforms 214, 216, 218 and 220, each containing a concave recess and serving as a deflector for fluid and cleaning solution expelled from a probe. After a probe dispenses its fluid into a reaction well in a cuvette, and before the probe is positioned to aspirate sample or reagent as the case may be, the probe is positioned over trough 210 for aspirating cleaning solution. The probe is then positioned over the corresponding deflector where primer fluid, such as water, is forced through the probe interior for expelling the cleaning solution, followed by primer liquid, against the deflector thereby creating a fountain effect which washes the outside of the probe. The waste solutions are captured by trough 212 and vented away through a waste outlet (not shown). A more detailed description of probe washing station 44 is described in the aforementioned U.S. Pat. No. 4,989,623 to Hoffman et al.

Figure 2:
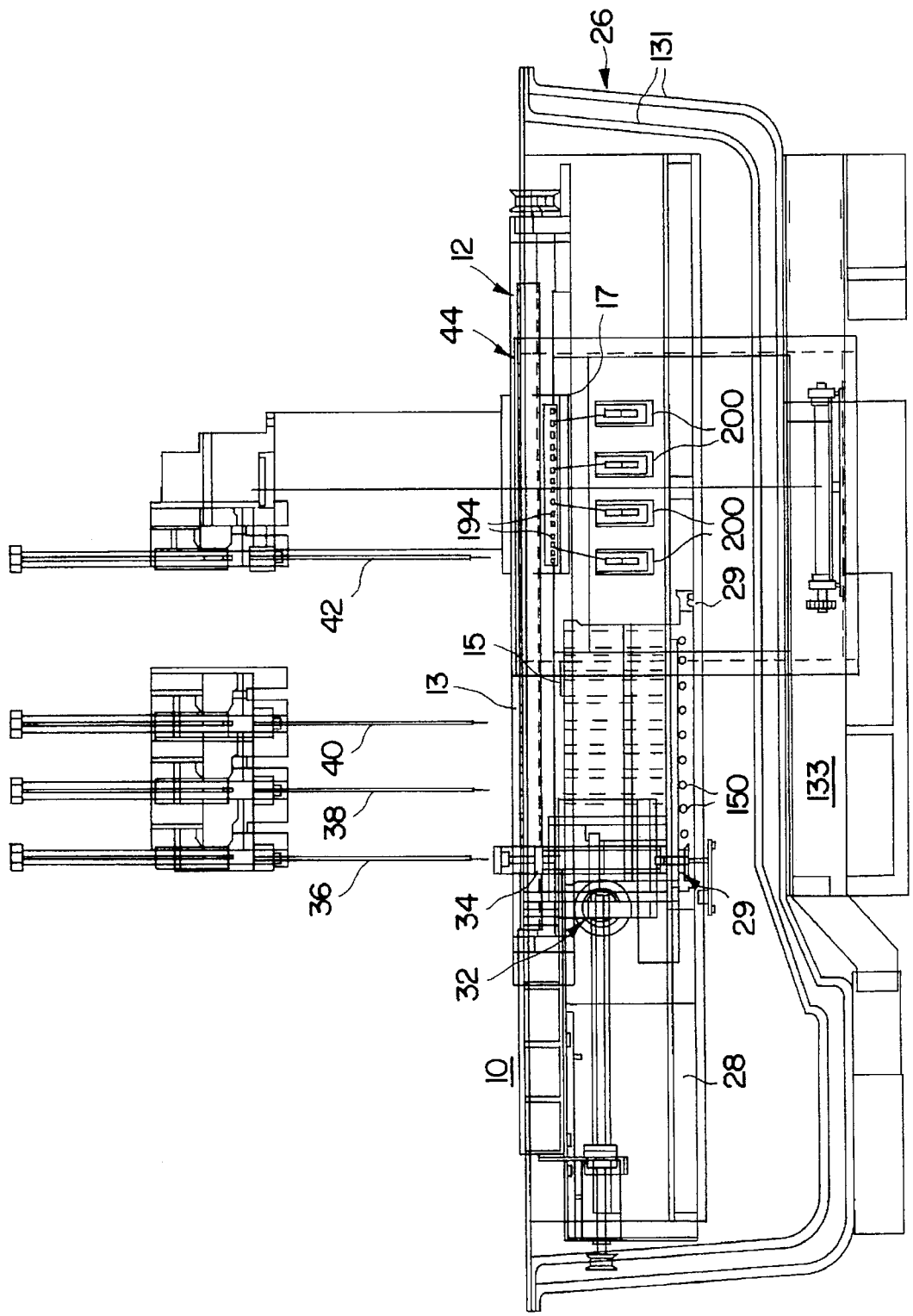
FIG. 2 is a schematic front elevation of FIG. 1.

Optical monitoring station 22 comprises a multichannel optical monitoring system of the type described in detail in the above-mentioned U.S. Pat. No. 5,002,392 to Swope et al. Briefly, and with reference to FIGS. 2 and 3, the optical monitoring system includes a broad band light source 182, which passes light through a slit (not shown). A collimating lens 184, collimates the beam to form a slowly diverging beam 186 which is folded by reflecting mirrors 188, 190 and 192. Following mirror 192 is a mask (not shown), which includes a plurality of linearly spaced apertures for dividing beam 186 into a corresponding number of beams, each defining an optical path or channel 194, as schematically illustrated in FIG. 2. The optical paths or channels 194 are linearally spaced along the track of cuvette transport mechanism 12 so that each reaction well of a cuvette passes from channel-to-channel as cuvette transport mechanism 12 incrementally advances the cuvettes along the linear path. The light beams passing through the reaction wells of the cuvettes are passed through a rotating shutter 194 which sequentially passes the light beams to diffraction gratings 196 where the beams are diffracted and focused by focusing lenses 198 onto respective photodiode arrays 200 which are subsequently electronically scanned for reading electronic signals which correspond to the spectral distribution of the beams transmitted by the respective reaction volumes contained in the reaction wells of the cuvettes. In one specific implementation, the optical monitoring system includes 20 channels, and the rotating shutter operates to sequentially pass the beams within groups of five beams, so that only one beam from each group of five beams is passed onto a photodiode array at any one time. The focusing lenses operate to focus each group of five beams onto a respective one of photodiode arrays 200.

The invention will now be described more particularly in connection with coagulation, chromogenic and immunological testing.

I. Specimen Handling

The present invention automatically handles the sample to be tested from the moment the collection tube containing the sample is placed in the analyzer. The analyzer has a first transporting device for transporting the sample collection tubes, in order, first to the programming station and then to the sample insertion station and a second transporting device for transporting the cuvettes through the sample insertion station, the reagent station and on to the optical monitoring device where the optical characteristics of the reaction volume in the respective reaction wells can be monitored.

According to a preferred embodiment of the invention, the sample collection tubes are evacuated and sealed by a septum, the tubes are sampled with a piercing/aspirating sample probe which deposits the proper amount of sample into the well of a cuvette. The preferred cuvette is described in Karp et al. US Des. 325,090 and U.S. Pat. No. 5,040,894.

According to another aspect of the invention, the temperature controlled housing maintains the temperature of the evacuated collection tubes and the reagent containers between 9° C. and 15° C.

Further, the second transporting device preferably includes a linear track for guiding the cuvettes and a drive mechanism for periodically moving the cuvettes along the track in discrete increments. Preferably, the drive mechanism includes a lead screw and the cuvettes are each shaped for engaging the lead screw for being driven along the linear track in the manner described in the above referenced U.S. Pat. No. 5,040,894. According to yet a further aspect of the invention, the cuvette storage includes a device for removing the cuvettes from the storage and placing the cuvettes onto the linear track.

Additionally, the first transporting device preferably includes a plurality of shuttles each for holding a plurality of sample collection tubes and means for moving the shuttles through the programming and sample insertion stations.

Each sample is given a machine-readable identification, such as a bar code, which is used in assay entry and during tracking of the assay. For example, a freshly drawn tube of blood is manually labelled with a bar code, and the bar code, patient identification and required tests are manually entered into the analyzer's computer. The tube is then placed into a shuttle and the shuttle placed in the shuttle storage area, where its bar code is automatically read by the analyzer and tracked by the quality control programming. The septum is pierced with the sampling probe, called Probe 1, which has been programmed as defined in the adf, to withdraw a specified amount of sample from the tube or collection device, which proceeds to aspirate the sample and dispense it into a predetermined well of a predetermined cuvette. The probe is then washed in order to remove essentially all of the sample remaining on it, in order to avoid cross-contaminating the next sample. Wash solutions include, among others, water, bleach solutions, preferably a 10% bleach solution, or specifically formulated wash solutions that are capable of removing essentially all of the sample from the probe. At times later in the assay, each probe can be washed after each use, for the same reasons. However, another reason for washing a probe is because in these types of assays, should thrombin, thromboplastin or phospholipids contaminate the probe, they are extremely difficult to remove, and thereby contaminate the next assay well. Removal of these extremely sticky substances from the probe is needed for both the method and the instrument to perform.

The analyzer has been programmed so that this particular well will have a specific assay performed in it. The quality assurance program tracks the well at specified times throughout the test procedure, confirming assay identification, correct volume delivery, correct adf interpretation and proper temperature control at critical times.

Preanalytical variables, such as the presence of hemolysis, bilirubin, lipemia, and fibrin clots are determined in conjunction with the performance of an assay. This is accomplished by utilizing a bichromatic technique inspecting a baseline wavelength and wavelength where the substance of interest can be detected. Unique algorithms are then applied to quantitate each substance. For example, hemolysis is detected by monitoring transmittance at 535 nm and 515 nm and computing a hemolysis index, which is $$\text{Hemolysis Index } (HI) = \frac{\text{Normalized transmittance at 535 nm}}{\text{Normalized transmittance at 515 nm}}$$

The heme unit of the hemoglobin molecule has adsorption at the 535 nm band pass (see FIG. 1).

Bilirubin is conducted the same way but uses 450 nm and 710 nm as the wavelengths of interest, while lipemia is measured by monitoring the normalized transmittance at 710 nm.

II. Sample Preparation

The next step is the automatic preparation of the sample for testing. This includes the ability of the analyzer to access any reagent and to deposit it in a cuvette well; to wash the probe through which the reagent is accessed after each reagent is dispensed with a wash solution as described above in order to avoid cross-contamination problems between reagents or reagents and samples; a universal profile testing method for all coagulation assays; a means for automatically diluting the sample; and a means for monitoring levels of the reagents and samples in their cuvettes and tubes.

The random access movement of the probes is used to aspirate and dispense reagents and samples according to test protocol for a particular assay (defined by the adf parameters), ordered or scheduled from the bar code of a given sample collection tube. This movement, and a description of the analyzers instrumentation, is more fully explained in the co-pending parent application, U.S. Ser. No. 07/833,950. Correct reagent/plasma volume delivery is monitored through the use of a novel dye tracking system, one type of which is described in U.S. Pat. No. 5,068,181. The versatility provided by the presence of adf's allow the fully automated analyzer to be optimized for each specific assay, allowing for the flexibility required for radically different assay formats. Below are diagrams of adfs for three assays (Tables 1–3), Factor VIII reference curves, PT and plasminogen reference curves. The first column notations A1, A2, A3 and A4 refer to the automated arms of the analyzer, the second column notations refer to various operations, such as pumping velocity, dilution, and aspiration. The numbers after the colons are the editable parameters, dealing with each of the various operations, such as volume amount or number of dilutions or velocity. A number of 000 means that no function is performed by the particular arm at that particular point in time. The notations after A4 refer to the optical set-up of the analyzer.

TABLE 1 adf Parameters for FVIII Ref. Curves

| | | | |
|---|---|---|---|
| A1 Run Volume | : 50 | A3 Reagent Volume | : 051 |
| A1 Pump Velocity | : 1000 | A3 Reagent Airslug | : 040 |
| A1 Sample Location | : 001 | A3 Pump Velocity | : 1250 |
| A1 Sampling Macro | : SFSTASP | A3 Reagent Location | : 001 |
| A1 Dilution Count | : 007 | A3 Fetch Macro | :FETCH2 |
| A1 Dilution Mix (1:x) | : 010 | A3 Deliver Macro | :DELREAGENT |
| A1 Dilution Sample | : 010 | A3 Wash/Rinse Macro | : WASH |
| A1 Dilution Primer | : 090 | A3 Cleaner Volume | : 005 |
| A1 Dilution Aspirate | : 050 | A3 Cleaner AirSlug | : 085 |
| A1 Dilution Macro | : SMIDASP | A3 Rinse Volume | : 800 |
| A1 Non-Serial Dilution Count | : 000 | | |
| A1 Wash/Rinse Macro | : RINSEP | A4 Reagent Volume | : 051 |
| A1 Cleaner Volume | : 000 | A4 Reagent AirSlug | : 040 |
| A1 Cleaner AirSlug | : 000 | A4 Pump Velocity | : 1500 |
| A1 Rinse Volume | : 800 | A4 Reagent Location | : 002 |
| | | A4 Fetch Macro | : FETCH2 |
| A2 Dilution Volume | : 051 | A4 Deliver Macro | : DELOPTICS |
| A2 Primer Volume | : 000 | A4 Wash/Rinse Macro | : WASH |
| A2 Aspirate Volume | : 000 | A4 Cleaner Volume | : 005 |
| A2 Dilution AirSlug | : 010 | A4 Cleaner AirSlug | : 085 |
| A2 Pump Velocity | : 1000 | A4 Rinse Volume | : 800 |
| A2 Buffer Location | : 005 | Assay Blank time | : 007 |
| A2 Dilution Macro | : FETCHOEL | Assay Maximum Time | : 240 |
| A2 Dilution Count | : 000 | Normalization Value | : 3000 |
| A2 Dilution Concentrat | : 000 | Replicate Count | : 000 |
| A2 Dilution Mix (1:x) | : 000 | Wavelength Count | : 003 |
| A2 Non-Serial Dilution Count | : 000 | 5, 15, 20 | |
| | | Dltm Recalc Override | : 0000 |
| A2 Throw Away Volume | : 000 | Spare 2 | : 0000 |
| A2 Middle Dilution | : 000 | Spare 3 | : 0000 |
| A2 Middle Primer Vol | : 000 | Spare 4 | : 0000 |
| A2 Middle Aspirate Vol | : 000 | Spare 5 | : 0000 |
| A2 Middle Dilution Macro | : | | |
| A2 Wash/Rinse Macro | : RINSEP | | |
| A2 Cleaner Volume | : 000 | ADF Name | : FVIIIR.ADF |
| A2 Cleaner AirSlug | : 000 | | |
| A2 Rinse Volume | : 800 | | |

TABLE 2 adf Parameters for PT

| | | | |
|---|---|---|---|
| A1 Run Volume | : 51 | A3 Reagent Volume | : 000 |
| A1 Pump Velocity | : 1000 | A3 Reagent Airslug | : 000 |
| A1 Sample Location | : 001 | A3 Pump Velocity | : 0000 |
| A1 Sampling Macro | : PIEREC | A3 Reagent Location | : 000 |
| A1 Dilution Count | : 000 | A3 Fetch Macro | : |
| A1 Dilution Mix (1:x) | : 000 | A3 Deliver Macro | : |
| A1 Dilution Sample | : 000 | A3 Wash/Rinse Macro | : |
| A1 Dilution Primer | : 000 | A3 Cleaner Volume | : 000 |
| A1 Dilution Aspirate | : 000 | A3 Cleaner AirSlug | : 000 |
| A1 Dilution Macro | : | A3 Rinse Volume | : 000 |
| A1 Non-Serial Dilution Count | : 000 | | |
| A1 Wash/Rinse Macro | : RINSEP | A4 Reagent Volume | : 101 |
| A1 Cleaner Volume | : 000 | A4 Reagent AirSlug | : 040 |
| A1 Cleaner AirSlug | : 000 | A4 Pump Velocity | : 1250 |
| A1 Rinse Volume | : 800 | A4 Reagent Location | : 001 |
| | | A4 Fetch Macro | : FETCH3 |
| A2 Dilution Volume | : 000 | A4 Deliver Macro | : DELOPTICS3 |
| A2 Primer Volume | : 000 | A4 Wash/Rinse Macro | : WASH1 |
| A2 Aspirate Volume | : 000 | A4 Cleaner Volume | : 030 |
| A2 Dilution AirSlug | : 000 | A4 Cleaner AirSlug | : 115 |
| A2 Pump Velocity | : 0000 | A4 Rinse Volume | : 800 |
| A2 Buffer Location | : 000 | Assay Blank time | : 005 |

TABLE 2-continued adf Parameters for PT

| | | | |
|---|---|---|---|
| A2 Dilution Macro | : | Assay Maximum Time | : 150 |
| A2 Dilution Count | : 000 | Normalization Value | : 3000 |
| A2 Dilution Concentrat | : 000 | Replicate Count | : 000 |
| A2 Dilution Mix (1:x) | : 000 | Wavelength Count | : 003 |
| A2 Non-Serial Dilution Count | : 000 | 5, 15, 20 | |
| | | Dltn Recalc Override | : 0000 |
| A2 Throw Away Volume | : 000 | Spare 2 | : 0000 |
| A2 Middle Dilution | : 000 | Spare 3 | : 0000 |
| A2 Middle Primer Vol | : 000 | Spare 4 | : 0000 |
| A2 Middle Aspirate Vol | : 000 | Spare 5 | : 0000 |
| A2 Middle Dilution Macro | : | | |
| A2 Wash/Rinse Macro | : | | |
| A2 Cleaner Volume | : 000 | ADF Name | : PT.ADF |
| A2 Cleaner AirSlug | : 000 | | |
| A2 Rinse Volume | : 000 | | |

TABLE 3 adf Parameters for Plasminogen

| | | | |
|---|---|---|---|
| A1 Run Volume | : 50 | A3 Reagent Volume | : 050 |
| A1 Pump Velocity | : 1500 | A3 Reagent Airslug | : 005 |
| A1 Sample Location | : 001 | A3 Pump Velocity | : 1250 |
| A1 Sampling Macro | : SFSTASP2 | A3 Reagent Location | : 004 |
| A1 Dilution Count | : 000 | A3 Fetch Macro | :FETCH1 |
| A1 Dilution Mix (1:x) | : 000 | A3 Deliver Macro | :DELREAGENT |
| A1 Dilution Sample | : 010 | A3 Wash/Rinse Macro | : WASH |
| A1 Dilution Primer | : 010 | A3 Cleaner Volume | : 010 |
| A1 Dilution Aspirate | : 000 | A3 Cleaner AirSlug | : 045 |
| A1 Dilution Macro | : | A3 Rinse Volume | : 800 |
| A1 Non-Serial Dilution Count | : 000 | | |
| A1 Wash/Rinse Macro | : RINSEP | A4 Reagent Volume | : 050 |
| A1 Cleaner Volume | : 000 | A4 Reagent AirSlug | : 040 |
| A1 Cleaner AirSlug | : 000 | A4 Pump Velocity | : 1500 |
| A1 Rinse Volume | : 800 | A4 Reagent Location | : 004 |
| | | A4 Fetch Macro | : FETCH1 |
| A2 Dilution Volume | : 040 | A4 Deliver Macro | : DELOPTICS |
| A2 Primer Volume | : 140 | A4 Wash/Rinse Macro | : WASH |
| A2 Aspirate Volume | : 155 | A4 Cleaner Volume | : 010 |
| A2 Dilution AirSlug | : 000 | A4 Cleaner AirSlug | : 080 |
| A2 Pump Velocity | : 1600 | A4 Rinse Volume | : 800 |
| A2 Buffer Location | : 003 | Assay Blank time | : 005 |
| A2 Dilution Macro | : BFSTRA | Assay Maximum Time | : 060 |
| A2 Dilution Count | : 002 | Normalization Value | : 3000 |
| A2 Dilution Concentrat | : 005 | Replicate Count | : 000 |
| A2 Dilution Mix (1:x) | : 020 | Wavelength Count | : 003 |
| A2 Non-Serial Dilution Count | : 001 | 2, 3, 34 | |
| | | Dltn Recalc Override | : 0001 |
| A2 Throw Away Volume | : 100 | Spare 2 | : 0000 |
| A2 Middle Dilution | : 010 | Spare 3 | : 0000 |
| A2 Middle Primer Vol | : 040 | Spare 4 | : 0000 |
| A2 Middle Aspirate Vol | : 050 | Spare 5 | : 0000 |
| A2 Middle Dilution Macro | : BMIDASP | | |
| A2 Wash/Rinse Macro | : RINSEC | | |
| A2 Cleaner Volume | : 000 | | |
| A2 Cleaner AirSlug | : 000 | | |
| A2 Rinse Volume | : 800 | | |

The universal testing profile is an extremely important part of this invention. All known coagulation analyzers, semi-automated and automated, perform on the basis that each test requires a unique profile. For example, only Prothrombin (PT) or only APTT assays are to be run at any given time as a batch, and therefore such machines are programmed to run the same way for each sample. They are incapable of doing a prothrombin time test on one sample and an APTT on the next, as the temperature vs. time parameters of each test are different. Some analyzers can perform multiple batch analysis simultaneously, but do not use the same profile. One way of doing so is being having unique pathways for each batch mode. The universal thrombosis and hemostasis temperature profile (temperature vs. time) is a method that allows all coagulation assays to be run through the same linear transport system using the same timing sequence, on the analyzer, to produce the necessary profile, with variables being the probe delivery temperatures and volumes, which are functions of parameters established by the adf.

The universal profile represents a balance between the different thermal requirements for each assay. This allows coagulation assays to be performed in a continuous, fully automated format.

There are nine critical requirements of the preferred universal thrombosis and hemostasis profile:

1. The temperature of the sample dispensed into the cuvette is preferably between about 4° C. and about 25° C.

2. The sample must remain in a temperature range of from about 4° C. to about 25° C. until the heating sequence begins.

3. The time required to warm the sample temperature from the pre-ramp temperature range to the post-ramp temperature range is 80±10 seconds.

4. The temperature of the sample at the end of the ramp must be 33° C.±1° C.

5. If the test is an APTT, the activation reagent is added immediately at the end of the ramp (Arm 3).

6. The temperature of the reagent delivered at R1 is 40° C.±1° C., raising the reaction temperature to 37° C.

7. If the test is a PT, the sample must reach 37° C.±1° C. in 120±10 seconds after the 80 second ramp segment (Arm 4).

The temperature of the reagent delivered at R2 is 37° C.±1° C.

9. The temperature of the mixture must remain at 37° C.±1° C. for at least 360 seconds after R2.

These temperature and time controls occur due to the interaction of the heated probes that aspirate and dispense liquids, which are described in more detail in U.S. Pat. No. 5,178,019 to Keiter, and the portion of the sample handling system, the heating and cooling track, as described in U.S. Ser. No. 07/833,950.

Figure 8:
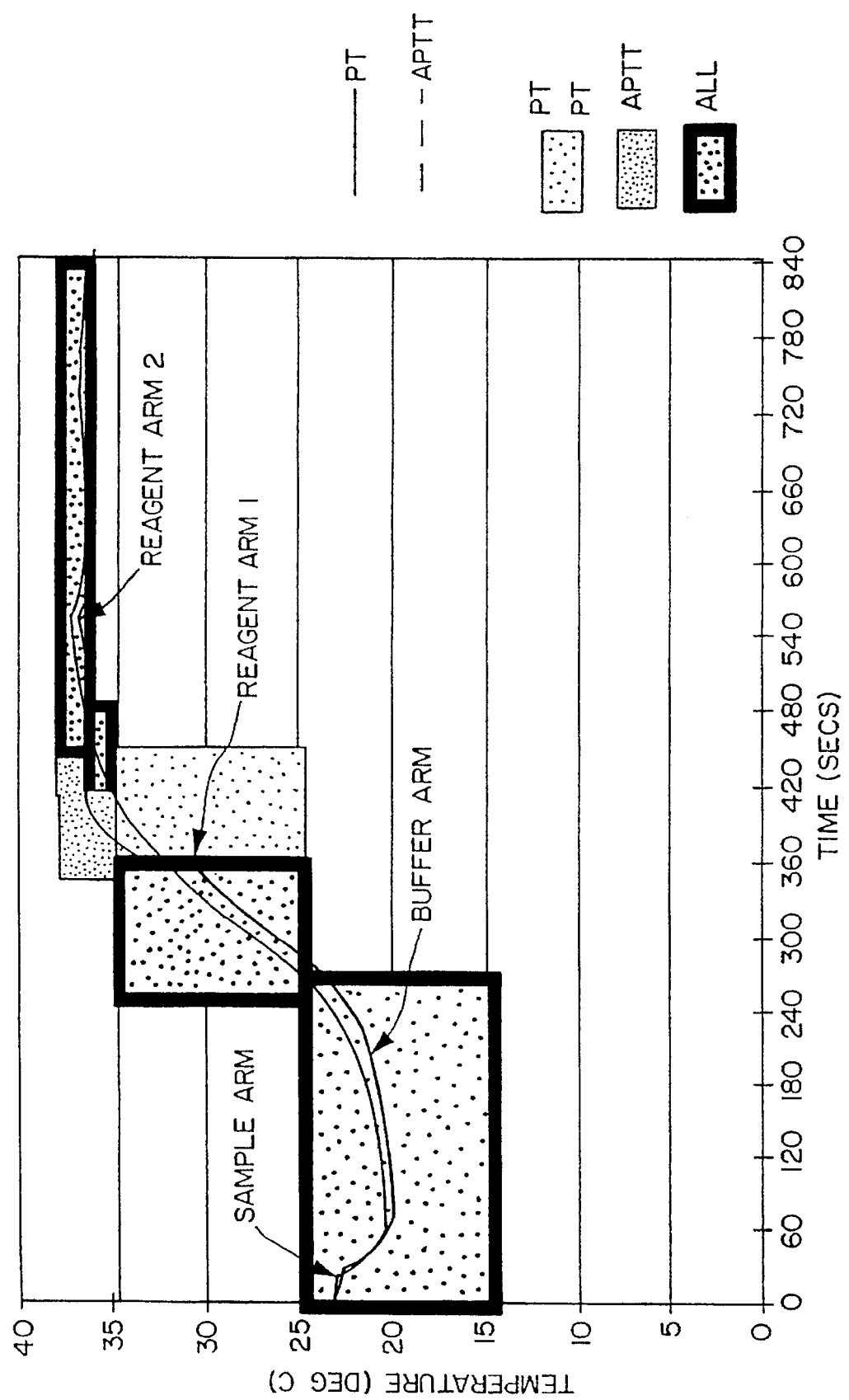
FIG. 8—The temperature of a sample is shown for a PT assay definition and an APTT assay definition as a function of time. Each sample/reagent delivery location is identified. The acceptable temperature ranges at each instant in the temperature profile are identified by "zones."

Flexibility in the adf allows for minor changes in temperature profiles that allow for the total optimization of each assay. Diagrams of the profile and optimization ranges for the PT and APTT assays are attached (see FIG. 8).

Figure 9:
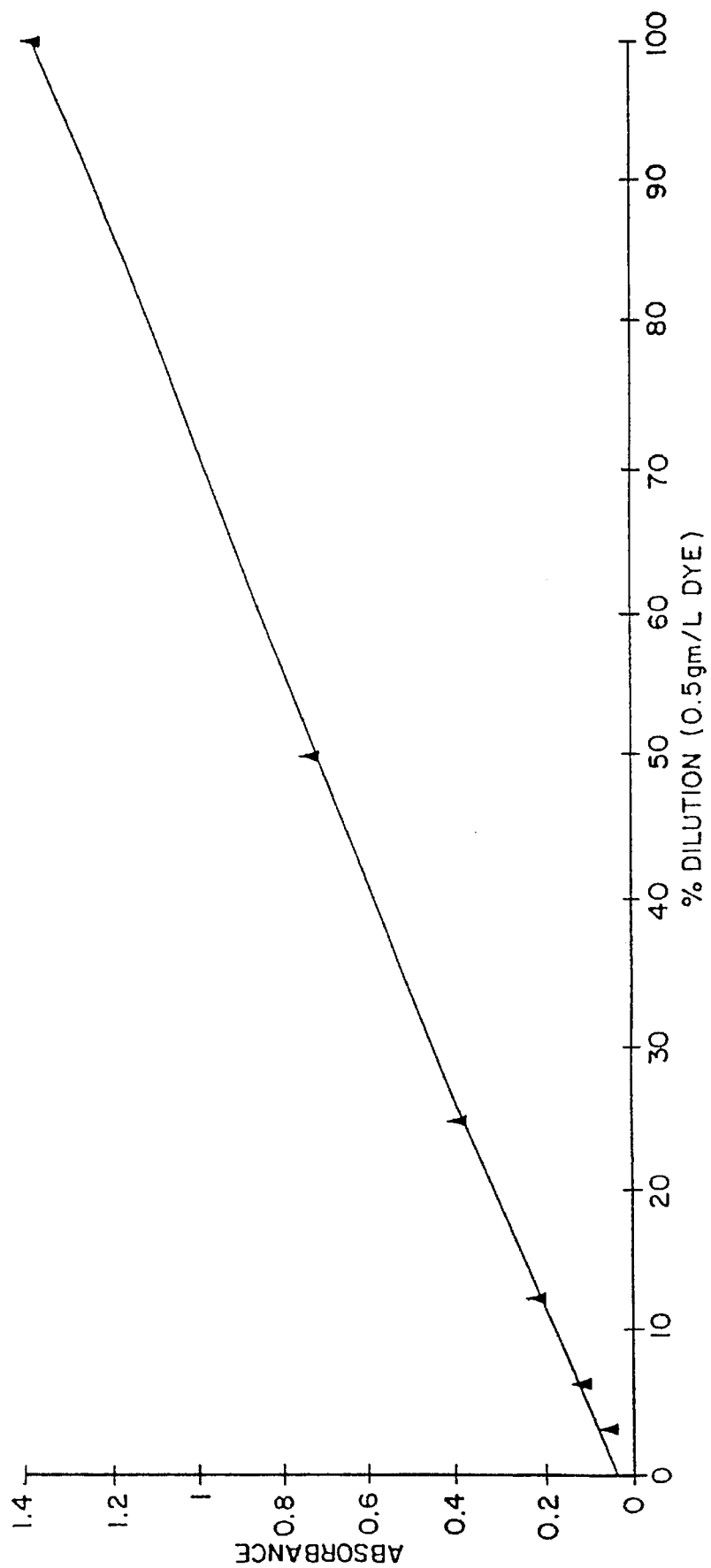
FIG. 9 shows the relative absorbance rates of a dye sample, serially diluted. A Least Squares regression line is also shown, and its goodness-of-fit measure $r^2$.

Another aspect of the sample preparation segment of the automatic coagulation analyzer is a means to automatically dilute samples. The analyzer performs a wide range of serial and nonserial dilutions for a large set of assays in a real time format. The adf for each complex method (methods requiring dilutions) defines the dilution: serial and non-serial, which buffers to use, how to dilute concentrated buffers and which arm to perform the dilution on (arm 1 or 2). Successful dilutions are a function of fluidic movement, probe design and robotic design. In addition, the analyzer, with its built-in quality control and quality assurance programming, ensures the accuracy of the dilutions. FIG. 9 shows the relative absorbance rates of a dye sample, serially diluted. A least squares regression line is also shown, and its goodness-of-fit measure $r^2$.

Finally, the analyzer provides a means for monitoring levels of the reagents in their containers and of the samples in their sample tubes or holding devices. This is another necessary function for a fully automated analyzer, as an assay cannot be performed without the proper amount of reagents. In the present analyzer, a reagent chamber holds a large number of reagent containers, at a temperature of about 7° C., and some reagents may be automatically mixed to maintain a homogeneous suspension. If necessary, the reagent is heated in the probe before dispensing. Fluid level sensing is used to control the height of a reagent probe relative to the level of a reagent in its container.

III. Optical Inspection

Once the reagents are added to the test sample, the reaction, if any, is read through spectrophotometric means. The optical inspection segment of the analyzer consists of a means for multiple wavelength analysis; a means to continuously normalize the fluctuations in light levels associated with sample to sample variability; and a means for using a broad spectrum of wavelengths in order to read the results of a variety of test reactions at the appropriate wavelength for that test.

As stated above, a preferred format of these functions are well-described in U.S. Pat. No. 5,002,392 and U.S. Ser. No. 07/869,579.

The quality control programming insures proper wavelength selection by monitoring the signal noise to ratio for each sample as defined in the adf. If the signal to noise threshold is exceeded then another wavelength is used. If all wavelengths are unacceptable then an error flag is provided to the user.

The quality assurance programming assures that the true wavelength is being evaluated by incorporating a piece of spectral glass with known absorbance characteristics. The peaks are measured by the analyzer and compared to the known values. Furthermore, a liquid crystal clot simulator has been incorporated into the optics module that when properly stimulated creates a signal that is similar to a clot. The output is inspected to insure the integrity of the optics unit as well as the integrity of the analysis algorithms.

IV. Signal Processing

The signal processing segment of the analyzer is the segment that reports the results of the assays. The analyzer has the ability to determine kinetic endpoints; to do multi-rule analysis of the final test results; to perform complex processing that determines endpoints other than clot formation; and provides an on-line database against which each test result can be compared.

An endpoint algorithm library is required to facilitate the analysis of the different types of assays. The major categories of endpoint analysis are linear rates, logarithmic rates, relative magnitudes and kinetic endpoints based on the biological characteristics of multianalyte mixtures (i.e., clot formation).

For example, the standard way of determining a PT or APTT clotting time is to take a sample, add the appropriate reagents and visually or spectrophotometrically determine when a clot has formed. When visually inspecting a sample for clot formation, the sample will turn more turbid after a clot has formed. Semi-automated analyzers set an endpoint at an arbitrary level of light reduction that is somewhat equitable to the visual method. However, this method is susceptible to error due to the presence of mechanical, optical, electrical and biological artifacts. Furthermore, as the instrument "ages", decreases in light transmission can result in a shift in the endpoint times.

Visual clot formulation occurs when the specimen mixture turns turbid. This can be physiologically associated with the initial conversion of fibrinogen to fibrin. (See, E. Ludvigh, "Perception of Contour," Bureau of Medicine and Surgery, Proj. No. NM001 075.01.04, Aug. 17, 1953.) The maximum rate of acceleration, the time of the peak of the second derivative, is indicative of the initial fibrinogen, fibrin conversion and directly correlates to a visual method (see FIG. 11). Because the time is computed on a data stream that is independent of arbitrary thresholds the usual artifacts associated with the instrument and biologics are negated resulting in more accurate and precise results. The same approach of analyzing characteristics of the signal stream for unique parameters is applied to the calculation of rate and magnitude for chromogenic, immunologic and quantitative fibrinogen assays.

For complex assays, kinetic endpoint results, such as clot times and reaction rates, additional processing is required. In these assays, the desired reported value of a sample is a function of some reference curve, which relates a quantity of a known analyte to reported endpoint values. Typically, a series of endpoint-based tests are performed on a series of concentrations from dilutions of a reference material. The paired data sets of recovered and reported values are then used to construct the reference curve.

The reference curve represents a function which is a model built using the sample data. (See, "Computer Evaluation of Reference Curves for the Estimation of Extrinsic Coagulation Factors," Frank et al., *Comput Biol Med*, Jan 1978). Traditionally, these functions have been assumed to be of a form similar to i f(recovered value)=$a_1$g(reported value)+$a_0$ where f(), g() are typically $\log_{10}$(). This function is particularly easy to represent graphically by hand, and numerically the coefficients can be recovered by simple linear regression using the formulas, $$\text{slope} = \frac{n\Sigma xy - (\Sigma x)(\Sigma y)}{n\Sigma x^2 - (\Sigma x)^2}$$

intercept=$\bar{Y}$–slope $\bar{X}$

This type of function, while seemingly accurate, especially when calculated graphically by hand, is not representative of the true biological processes and leads to errors because points deviating from a straight line on a log-log reference curve are thought to deviate by random error and are neglected.

These simple functions restrict the degrees of freedom necessary to accurate model coagulation assays, which are more complex than simple chemical determinations based on known formulas. There are agents present in addition to the analyte of interest that complicate the cause-effect relationship.

The methods available in this invention allow for more flexibility in designing a model of the reference function which relates the desired reported results with recovered values. These functions provide a more accurate representation of the shape of the reference curve for each assay, accommodating unknown extraneous agents, which leads to more accurate and precise results; also provide robustness in the presence of small errors in the data; gives accurate representation of all sample data, without neglecting points; and providing for an increased range of reference recovery due to incorporation of all dilutions, including those that were once ignored due to deviation from the straight line.

Three methods that are generally used to create models from experimental data are: (1) Gauss Jordan and (2) Singular Value Decomposition (SVD) for linear systems, and (3) Levenberg-Marquardt Method for non-linear systems. Gauss-Jordan is generally considered a simpler, but less accurate method for solving linear systems. Singular-Value is more costly in terms of number of operations, but it has the advantages of being more accurate, and is robust in the presence of singularities, where Gauss-Jordan cannot function. These singularities are approached when there are two solutions very close together, which is not uncommon. The error creeps into Gauss-Jordan when two very large numbers cancel each other when there is a very small pivot (i.e., close to singular). The accuracy of SVD and Levenberg-Marquardt methods are comparable.

The general form of a linear (in its coefficients) data model is $$y(x) = \sum_{k=1}^{M} a_k X_k(x).$$

The merit function typically used to determine the best set of parameters $a_k$ is $$\chi^2 = \sum_{i=1}^{N} \left[ \frac{y_i - \Sigma_{k=1}^{M} a_k X_k(x_i)}{\sigma_i} \right]^2.$$

The minimum of this function is found where the derivative of $\chi^2$ with respect to all M parameters $a_k$=0, which leads to what are known as the normal equations, or a linear system $$\sum_{j=1}^{M} \left[ \sum_{i=1}^{N} \frac{X_j(x_i)X_k(x_i)}{\sigma_i^2} \right]_{kj} a_j = \left[ \sum_{i=1}^{N} \frac{y_i X_k(x_i)}{\sigma_i^2} \right]_k.$$

In order to provide flexibility in determining the optimum reference function for each assay, several components were made available in the complex data analysis module:

A variety of data transformations, i.e., log10, 1/, etc.;
switching the x and y variables;
Polynomials of any order; and
Piecewise fitting, including overlapping.

The general form of the functions is $$f(y) = c_0 + c_1 f(x) + c_2 f(x)^2 \ldots c_n f(x)^n$$

where $$f(x) = x, \frac{1}{x}, \frac{1}{f(x)}, \log(x) \ldots$$

The "piecewise" form is $$f(y) = [f_1(x)]_{x=a}^{x=b}, [f_2(x)]_{x=b}^{x=c}, \ldots [f_n(x)]_{x=g}^{x=h}$$

where each "subfunction" can be a different type base on any combination of the sample data. Having the ability to select from the above options, an optimum reference function was selected for each complex assay. These optimized reference functions improve both the accuracy and precision of the assays. Each method was tested to determine if samples with known reported values were reported accurately, if diluted samples resulted in reported values at the expected levels, and if the sample data were fit well ($R^2$).

V. Quality Assurance

An important part of the quality control package is the use of statistical quality control rules applied to test data. This is very similar to the tests originally utilized for clinical chemistry quality control programs, known as the Westgard multirule systems but that have been applied to coagulation assays (See, Westgard, J., Wiebe, D., "Cholesterol Operational Process Specifications for Assuring the Quality Required by CLIA Proficiency Testing," *Clinical Chemistry*, Vol. 37, No. 11, pp. 1938–1944, 1991; and Westgard, J., Peterson, P., Wiebe, D., "Laboratory Process Specifications for Assuring Quality in the U.S. National Cholesterol Education Program," *Clinical Chemistry*, Vol. 37, No. 5, pp 656–661, 1991). This is available for use in two portions of the analyzer, the system quality control program and the on-line test quality control.

The system quality control defaults to a new control run mode when the allotted time designated for control run frequency is reached. The system pauses for the control run, which can only be overridden when an emergency sample is requested. Once the controls are assayed, the statistical quality control rule chosen is activated to interpret the results of the controls. If data passes the rules, quality control results are printed on a hard copy while being simultaneously saved to the on-board computer. If data violates any of the rules, it is flagged through a hard copy and the analyzer's monitor. The user has an option to either repeat the control, troubleshoot the cause of the flag or accept flagged control values.

A preferred variation of statistical rule data structure is shown in the following Table 4.

TABLE 4

Statistical Rules Data Structure

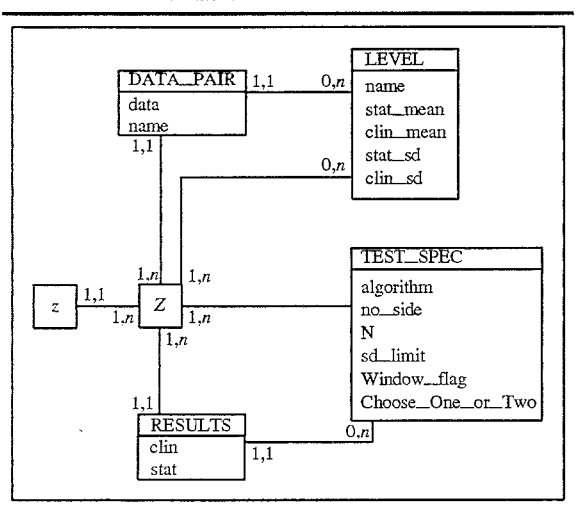

The purpose of the statistical quality control rules is to take an array of raw data (which may include data from several different controls or levels) and apply a set of tests to it. The set of tests, if chosen properly can have a very low false rejection rate coupled with a very high probability of rejection of bad results. Before the tests are applied to the data, they are converted to z-scores (normalized) using the level data, allowing different controls to be analyzed together. There can be any number of tests in a statistical rule, and a pair of results is returned for each individual test: one based on clinically significant ranges and one based on statistically significant ranges. Any number of raw data points may be used, as the rules assume that all of the data is to be examined. If GROUP window_flag is selected, the data will be divided into n/N groups. If SLIDING window_flag is chosen, the data will be arranged into (n–N) groups, each group starting at one point past the previous. One test result is returned for all groups—if one group fails, FAILED is the result returned; if all groups pass, PASSED is the result returned. In the case of GROUP and n not divisible by N, the last remaining points are ignored. All data selection is done external to multirules. If there is a "missing point" or if "historical data" is required, it is taken care of before the function is called, in the database query, or its equivalent. In the unexpected case of a set of rules having N's without a common denominator, a group of statistical rules can be used. This can be accomplished by building an object with multiple member statistical rules that returns the result of the cumulative result of its members.

The operation of the sample handling system will now be described in the context of one specific implementation of the invention, it being understood that the invention is not limited to this particular implementation.

Operation of the sample handling system according to the invention is centered on linear track 13 along which cuvettes are advanced from station to station by lead screw 88. The basic timing and sequencing of the system is based on advancing the cuvettes along the linear track a distance equal to the distance between successive reaction wells.

Initially, an operator loads cuvettes into the instrument by placing a cassette of cuvettes into cassette frame 46. Each cassette holds, for example, 120 cuvettes. The cuvettes are automatically moved from the cassette onto linear track 13 by arm 52 where they engage lead screw 88. Each cuvette preferably has four ¼ inch reaction wells. Lead screw 88 is activated every fifteen seconds to move the cuvettes in 0.25 inch increments in 0.1 seconds. The instrument controller monitors each cuvette by the timing associated with the lead screw. Lead screw 88 advances the cuvettes to the first station, i.e., sample insertion station 14, where a sample is delivered to a reaction well aligned with sample probe 36. Two minutes later, the reaction well of the cuvette arrives at the first reagent delivery probe 38 where diluent or a reagent is added, depending on the test being carried out. The second reagent probe 40 is located at the four minute position where an activator can be added. Five minutes later the loaded reaction well of the cuvette reaches the third reagent probe 42 where a reagent is added and the reaction monitoring begins. The reaction is monitored electro-optically by optical monitoring system 22 which measures changes in the optical transmission of the reaction volume as the clot forms or as the chromometric reaction proceeds. As the cuvette is moved along the track, the optical monitoring continues for twenty consecutive stations, that is, for 300 seconds. Following the optical monitoring station the cuvette leaves the track and is sent to a waste container (not shown).

Patient plasma samples are stored in refrigerated housing 26 in the original evacuated blood collection tubes used to obtain the patient's sample which has been previously spun down to obtain the plasma and bar-coded for patient identification and test protocol to be performed. The evacuated sample collection tubes are placed in the holders of shuttles 28 and advanced by the shuttle drive mechanism to the bar code reader. The evacuated sample collection tubes can be arranged in any order since the bar code on each sample collection tube allows the instrument to automatically correlate a patient with a given sample. The bar code read by bar code reader 32 also programs the instrument controller for determining the amount of sample to be aspirated by sample probe 36, the number of reaction wells to be filled with the sample, and the amounts and types of reagents/buffers/additives/activators to be injected into the respective reaction wells by reagent probes 38, 40 and 42. Subsequent to programming station 30, a sample collection tube is advanced to piercer 34 where piercing tube 152 is caused to pierce the septum of the evacuated sample tube to allow sample probe 36 to be lowered into the sample collection tube to aspirate a programmed amount of sample. Sample probe 36 is next removed from the evacuated sample collection tube and horizontally moved over a reaction well positioned at sample insertion station 14 and lowered into the reaction well where a programmed amount of sample is expelled into the reaction well. The evacuated sample collection tubes can be removed from refrigerated housing 26 at any time after sample aspiration is complete; however, because the samples are maintained at lowered temperatures, they can be retained for further testing without having to be immediately removed from its shuttle. Reagent chamber 35 stores various controls, diluents, activators and reagents. In one implementation of the system up to twenty-two containers of these materials are stored in reagent chamber 35. All containers are held to a temperature of about 7° C. and the reagents are heated, if necessary, in the reagent probe as they are being dispensed.

Pumping in all cases is performed with positive displacement syringe pumps operatively connected with respective ones of the probe. No manipulation of pump tubing is required as is the case with peristaltic pumps. A reagent is dispensed into a reaction well in a manner that promotes mixing with the sample and other contents of the reaction well. The reagent temperature and volume are controlled by the instrument controller.

Desirably, fluid level sensing is utilized to control the height of a reagent probe relative to the level of a reagent in its container and relative to the contents of a reaction well. This permits bringing the outside of a probe into contact with a minimum quantity of reagent. This, in turn, reduces the possibility for carry-over. Additionally, level sensing is used to control the height of a probe above the fluid level while dispensing in order to minimize carry-over and to maximize mixing.

At the same time that all of the above mechanical and programmed functions are occurring, various quality assurance/quality control checks are being automatically performed. Also, data calculations are being automatically performed in order to produce and deliver a final result of the parameter being assayed for. This is shown in the following example.

Example for Factor VIII on an Automated Analyzer

A Factor VIII assay was conducted to determine the relative quantity of the intrinsic pathway cofactor VIII (FVIII). FVIII concentration is critical in clot formation and deficiencies of it are symptomatic of a hemophiliac condition. It is important to be able to accurately quantitative the FVIII concentration in patient specimens. The invention addresses all aspects of properly performing the complex FVIII Assay.

A FVIII Assay consists of three types of sample evaluations:

1. Reference materials to normalize the reagent system.
2. Control materials to assure the quality of the reference curve.
3. Patient samples to aid in the diagnosis and treatment of the patient.

Specimen handling and dilutions (Arm 1)

The Factor VIII assay requires the dilution of sample (be it reference, control or patient) serially from a 1:5 to 1:1280. Each type of material requires a different set of dilutions that can be prescribed at time of sampling. The sample was diluted with imidazole buffer that was contained in the ARM1 reservoir. The Factor VIII reference curve was and is typically prepared as follows:

1. 90 uL of Imidazole was loaded into the syringe from the reservoir from arm 1.
2. The arm moved to the appropriate sample reservoir and aspirated 10 uL plasma.
3. The total 100 uL was delivered to the cuvette.
4. The probe then loaded 50 uL of Imidazole from the reservoir for arm 1.
5. 50 uL of the 100 uL was aspirated from the cuvette.
6. The track was incremented forward and the 50 uL aspirated from the previous well along with the 50 uL of Imidazole were delivered into the new well.
7. Steps 4 through 7 were repeated for each additional serial dilution required.

The end result was a FVIII reference curve with seven serial dilutions from a starting dilution of 1:10. The patient and control samples were diluted in the same fashion. Three serial dilutions were performed on a patient sample starting at 1:20, and 2 dilutions on the control material starting at 1:20. The system allows modification of the initial dilution ratio and the number of serial dilutions on a per patient basis.

Quality Checks: The ability to properly perform dilutions was verified using the dye verification process described in the sample preparation detailed description (See FIG. 9). If the plasma volume in the primary reservoirs is insufficient, a level sense error is generated. If insufficient volume for the Imidazole reservoir is detected, an error message is given.

Reagent Addition and Incubation

After the appropriate volume of plasma and buffer has been added to the test well, then the appropriate reagent must be added at the appropriate times to prepare the well for optical inspection.

Addition of factor deficient plasma (Arm 2):

The FVIII assay required the addition of 50 uL of Factor deficient material 2 minutes and 40 seconds after arm 1. The well was still maintained at ambient temperature.

Addition of Activator (Arm 3):

The FVIII assay is an APTT based assay (test of the intrinsic pathway) and required the addition of an activator material at arm 3 approximately 2 minutes and 40 seconds after the addition of the factor deficient material. During the 2 minutes and 40 seconds the test well is warmed from ambient temperature to about 33° C., then 50 uL of activator was added at 39° C. raising the temperature in the test well to 37° C. The activator was stored on the reagent tray at 8° C. and mixed automatically to maintain a homogenous suspension.

Addition of Calcium Chloride (Arm 4):

The sample was then incubated for 3 minutes 40 seconds at 37° C. The incubation/activation time is critical for clot based test measuring parameters of the intrinsic pathway. At the end of activation, 50 uL of 0.25 M calcium chloride was added at 37° C., starting the reaction.

Quality Checks: The correct volumes of reagents delivered was assured by the dye tracking system. The quality of the reagents was assured by using the multirule analysis quality control program defined earlier. The thermal profile was monitored by querying temperature sensors as a test well goes over them. If the temperature is determined to be out of range then an error message is reported to the user.

Optical Inspection

The test well was optically inspected for up to 300 seconds. During this inspection process the test well was exposed to fifteen different optical windows for 20 seconds each. A normalization process was required at the first optical windows that normalizes all other windows to the first. Additionally, the normalization process also removes the differences in light levels associated with variability due to the unique turbidity of each plasma. The data was collected for a unique set of assay specific wavelengths and stored in a data file. The data file also contained the data set required to determine quantities of preanalytical variables and dye concentrations for volume verification.

Quality Checks: There are quality checks for wavelength verification, optical integrity (Liquid Crystal Clot Simulator), and an acceptable signal to noise ratio as an indication of proper normalization.

Data Analysis

Endpoint determinations and calibrations:

All endpoints for the test well data files were computed using the peak of the second derivative described above. The endpoints were standardized using a unique calibration scheme. Systematic bias associated with reagent lot to lot variability and instrument to instrument variability was minimized by calibration of the system using labeled plasma calibrators. For more current coagulation systems, systematic error in the measurement of clotting times is due to instrument thermal and fluidic variation as well as in variation in reagent lot to lot sensitivity. Therefore, reference and therapeutic intervals are specific for each instrument and reagent lot and are routinely redetermined. The analyzer's calibration procedure normalized instrument mechanical variables and reagent inter-lot sensitivity, providing uniform APTT clotting times suitable for direct reporting or for use in standardization methods. The analyzer's APTT assays (including FVIII) were calibrated by replicate analysis of Verical Calibration Plasmas™ (Organon Teknika) that have assigned clotting times. Observed values were regressed versus assigned values and the resulting regression coefficients were used to normalize the instrument/reagent system.

Reference Curve Generation

Figure 10:
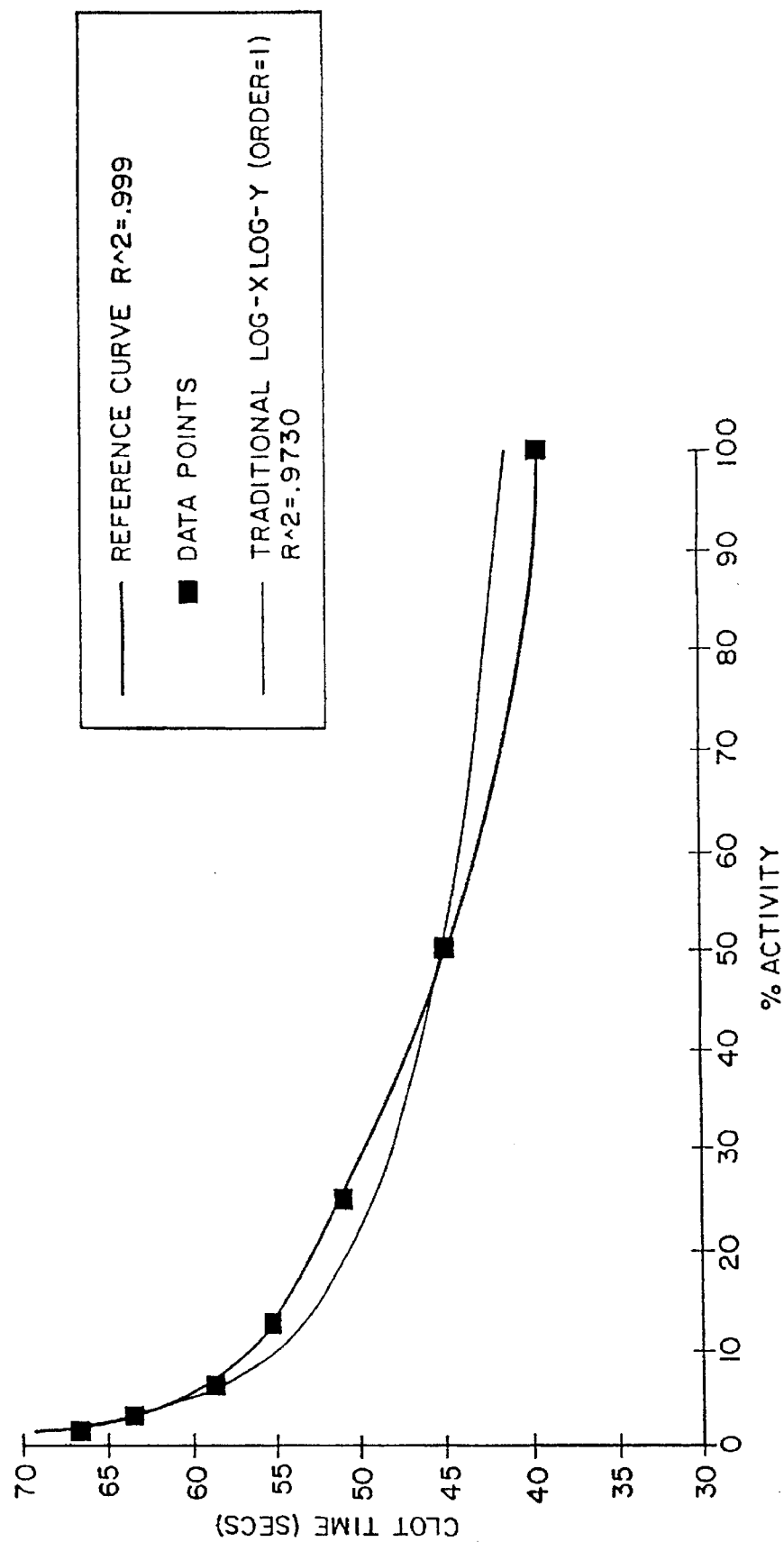
FIG. 10 shows the actual data points representing the clot times recovered for a serially diluted reference, and (1) the traditional curve and (2) the new curve fit through those points.

Reference curves were constructed by taking the dilution and known concentration of the reference material and regressing it with the obtained endpoint for each test well. The type of regression and analysis tool used dictates the quality of the reference curve and ultimately the quality of the patient result. The traditional method of constructing a Factor VIII reference curve, log-log transformation, fit to a first order polynomial is not representative of the true biological processes. The curve is better represented by the technique used for this invention. The improvements are most prevalent in the 50 to 100% range and 1 to 10% range, both ranges being clinically significant. The reference curve was constructed by plotting the % activity for the seven dilutions as the independent variable (x), and clotting time as the dependent variable (y). The function is piecewise and discontinuous and composed of two linear sub-curves fit to overlapping sets of data. The first sub-curve uses the first four dilutions and fits a second order polynomial to untransformed data. The second sub-curve fits a second order polynomial to log10 (clot times) and log10 (%activity) to all of the dilutions after the first one. A "cutoff", which determines which sub-curve is used to recover % activity, is established based on the clot time corresponding to the fourth dilution value recovered from the curve. The curve accurately represents the shape of the expected values, and remains robust in the presence of minor variance in the data. FIG. 10 shows a comparison between the traditional Factor VIII reference curve and the automatic analysis Factor VIII assay reference curve.

The patient samples were evaluated with respect to a stored or newly generated reference curve and the reported value was corrected for dilution automatically.

Quality Control Checks: Measures of Goodness of fit for the calibration process and the reference curve structure used were defined earlier. The control values were monitored and subjected to the quality control multirule analysis procedures. The slope of the sample dilutions when compared with the controls or reference curve are determined to assess for the presence of Factor VIII inhibitors such as the Bethesda inhibitor.

It will be understood that the above description of the present invention is susceptible to various modifications, changes and adaptations, and the same are intended to be comprehended within the meaning and range of equivalents of the appended claims.

We claim:

1. A method for performing qualitative and quantitative coagulation, chromogenic and immunological assays for hemostasis and thrombosis parameters on each of a multiplicity of samples of plasma, serum or whole blood, wherein each sample is selected for assay on a random access basis without a drop in speed of sample through-put, comprising:

a) identifying each of a multiplicity of samples, selecting each sample and scheduling one or more of a plurality of assays selected from each of qualitative and quantitative coagulation, chromogenic and immunological assays for hemostasis and thrombosis parameters, to be performed on each sample;

b) providing a plurality of test wells for said plurality of assays and a specimen handling means for automatically transferring at a sample insertion station an aliquot of each sample from a holding device to a respective test well of said plurality of test wells;

c) automatically selecting and adding reagents needed for said plurality of assays selected from each of qualitative and quantitative coagulation, chromogenic and immunological assays to measure hemostasis or thrombosis parameters of the samples in the test wells, wherein in a predetermined first constant time after the sample is delivered to the test well at the sample insertion station, the test well is disposed at a first reagent delivery probe station where a predetermined volume of reagent is optionally added to the test well depending upon the type of assay being performed on the sample in the test well, the volume and temperature of the reagent being variable depending upon which thrombosis or hemostasis assay is being performed;

and wherein in a predetermined second constant time after the test well passes through the first reagent delivery probe station, the test well is disposed at a second reagent delivery probe station where a predetermined volume of a second reagent is optionally added depending upon the type of assay being performed on the sample in the test well, the volume and temperature of the second reagent being variable depending upon which thrombosis or hemostasis assay is being performed;

and wherein in a predetermined third constant time after the test well passes through the second reagent delivery probe station, the test well reaches an optical monitoring station where a reaction of the sample and one or more reagents is monitored by an optical monitoring system for measuring changes in an optical transmission of the sample;

and wherein each of said predetermined constant times remains the same regardless of the hemostasis or thrombosis assay being performed on the sample;

said monitoring of the reaction of the sample comprising detecting the reaction in each test well and measuring data from each reaction, mathematically processing the measured data to evaluate a change in or magnitude of the measured data from the reaction in the well, and reporting results of the processing of the measured data.

2. The method according to claim 1, further comprising independently defining a test protocol for each assay.

3. The method according to claim 2, wherein the test protocol includes mechanical instructions, optical instructions, data analysis and quality assurance parameters.

4. The method according to claim 1, further comprising automatically diluting the transferred sample.

5. The method according to claim 1, further comprising:

a) controlling a cooling unit and maintaining each sample initially within a low temperature range having a predetermined maximum temperature;

b) controlling a heating unit that maintains each sample within a predetermined measuring temperature range that is higher than the initial temperature range;

c) transitioning the temperature of each sample from the initial range to the measuring temperature;

d) reducing an effect of ambient temperature on each sample; and e) delivering reagents to each test well at a specified temperature.

6. The method according to claim 1, wherein after dispensing a sample or reagent into a well, a sample preparation means for automatically selecting and adding the reagents for the scheduled assays is washed by a wash liquid.

7. The method according to claim 6, wherein the wash liquid is selected from a group consisting of water, wash solution and bleach solution.

8. The method according to claim 1, further comprising evaluating data obtained from each assay by a) calculating a second derivative of a process signal and determining the peak thereof, which is an indication of maximum acceleration of clot formation; or b) calculating a magnitude of change of a process signal; or c) calculating a rate of change of a parameter, whereby a first derivative of the parameter is determined; or d) a combination of the calculations of a)–c) above.

9. The method according to claim 1, wherein the data is transformed by normalization and calibration to standardized material by a numerical construction of a system model using known reference material, specific for each assay.

10. The method according to claim 9, further comprising a system model developed from a function with a linear or nonlinear relationship between recovered and reported values, the function created by fitting to a set of sample data.

11. The method according to claim 1, comprising a quality assurance protocol for monitoring and evaluating the sample handling, sample preparation, reaction detection and results reported for the sample, wherein the quality assurance protocol comprises checks for sample integrity, reagent integrity, mechanical suitability and optical quality.

12. The method according to claim 11, wherein the check for sample integrity comprises detecting at least one pre-analytical variable in the sample selected from lipemia, bilirubin and hemolysis.

13. The method according to claim 11, wherein the check for reagent integrity comprises evaluating control material and applying statistical quality control rules and a comparison of a current result to an earlier sample result.

14. The method according to claim 11, wherein the check for system suitability comprises measuring electrical, volumetric and thermal output of critical mechanical components.

15. The method according to claim 11, wherein the check for optical quality comprises monitoring an optical reference clot at an appropriate wavelength and monitoring the signal to noise ratio, thereby insuring the use of acceptable signals.

16. An instrument for automatically performing qualitative and quantitative coagulation, chromogenic and immunological assays for hemostasis and thrombosis parameters on each of a multiplicity of samples of plasma, serum or whole blood, whereby each sample is selected for assay on a random access basis without a drop in speed of sample through-put, comprising:

a) a programming input device for identifying each of a multiplicity of samples, and means for selecting each sample and scheduling one or more hemostasis and thrombosis assays to be performed on each sample on a random access basis;

b) a plurality of test wells for a plurality of assays and a specimen handling means for automatically transferring at a sample insertion station an aliquot of each sample from a holding device to a respective test well of said plurality of test wells;

c) a fully automated sample preparation means for automatically selecting and adding reagents needed for a plurality of qualitative and quantitative coagulation, chromogenic and immunological assays to measure hemostasis or thrombosis parameters of the samples in the test wells, a first reagent delivery probe station being provided where a diluent or reagent is optionally added to a test well depending upon the type of assay being performed on the sample in the test well, the test well being disposed at said first reagent delivery probe station in a predetermined first constant time after the sample is delivered to the test well at said sample insertion station, said sample preparation means comprising means for varying at said first reagent delivery probe station the type of reagent and the volume and temperature of the reagent depending upon which thrombosis or hemostasis assay is being performed;

a second reagent delivery probe station being provided where a reagent is optionally added depending upon the type of assay being performed on the particular sample in the test well, the test well being disposed at said second reagent delivery probe station in a predetermined second constant time after the test well passes through said first reagent delivery probe station, said sample preparation means comprising a means for varying at said second reagent delivery probe station the type of reagent and the volume and temperature of the reagent depending upon which thrombosis or hemostasis assay is being performed;

an optical monitoring station being provided where a reaction of the sample and one or more reagents is monitored by an optical monitoring system for measuring changes in the optical transmission of the sample, said test well reaching said optical monitoring station in a predetermined third constant time after the test well passes through said second reagent delivery probe station, and wherein each of said predetermined constant times remains the same regardless of the hemostasis or thrombosis assay being performed on the sample;

said optical monitoring system comprising a detector for detecting the reaction in each test well and measuring the data from each reaction, a processor for mathematically processing the measured data to evaluate a change in or magnitude of the measured data from the reaction in the well, and a reporter to report results of processing the measured data by the processor.

17. The instrument according to claim 16, wherein additionally is included a means for independently defining required steps for each assay.

18. The instrument according to claim 19, wherein instructions for a scheduled assay include mechanical instructions, optical instructions, data analysis and quality assurance parameters.

19. The instrument according to claim 16, wherein additionally is included a diluting device for automatically diluting the transferred sample.

20. The instrument according to claim 16, further comprising:

a) a cooling controller for independently controlling a cooling unit, maintaining each sample initially within a low temperature range having a predetermined maximum temperature;

b) a heating controller for independently controlling a heating unit that maintains each sample in an optically monitored section within the detector, within a predetermined measuring temperature range that is higher than the initial temperature range;

c) a transitioning device for transitioning each sample from the initial range to the measuring temperature;

d) a reducing device for reducing the effect of ambient temperature on each sample; and e) a transport mechanism for delivering reagents to the test well at a specified temperature.

21. The instrument according to claim 16, further comprising a washing mechanism wherein following each time a sample or reagent is dispensed into a well, the sample preparation means is washed by the washing mechanism with a wash liquid.

22. The instrument according to claim 21, wherein the wash liquid is selected from a group consisting of water, wash solution or bleach solutions.

23. The instrument according to claim 16, further comprising a computational means for evaluating data obtained from each assay, the computational means comprising:

a) means for calculating a second derivative of a process signal and determining the peak thereof, which is an indication of maximum acceleration of clot formation; or b) means for calculating a magnitude of change of a process signal; or c) means for calculating a rate of change of a parameter, whereby a first derivative of the parameter is determined; or d) a combination of the means for calculating of a)–c) above.

24. The instrument according to claim 16, wherein the change in or magnitude of the data is measured by a means for normalization and calibration to standardized material by a numerical construction of a system model using known reference material, specific for each assay.

25. The instrument according to claim 24, further comprising a system model developed from a function with a linear relationship between recovered and reported values, the function created by fitting to a set of sample data.

26. The instrument according to claim 16, wherein a quality assurance means is provided comprising a means for checking for sample integrity, reagent integrity, mechanical suitability and optical quality.

27. The instrument according to claim 26, wherein the means for checking for sample integrity comprises detecting preanalytical variables in the sample.

28. The instrument according to claim 26, wherein the means for checking for reagent integrity comprises evaluating control material and applying statistical quality control rules and a comparison of a current result to a earlier sample result.

29. The instrument according to claim 26, wherein the means for checking for mechanical suitability comprises a means for measuring electrical, volumetric and thermal output of mechanical components of said instrument.

30. The instrument according to claim 26, wherein the means for checking for optical quality comprises a means for monitoring an optical reference clot at an appropriate wavelength inspection and monitoring a signal to noise ratio.

31. The method of claim 1, wherein a plurality of cuvettes are provided, each comprising a plurality of said test wells, and wherein different assays selected from said qualitative and quantitative coagulation, chromogenic and immunological assays for measuring hemostasis or thrombosis parameters are performed on one or more samples in different test wells of the same cuvette.

32. The method of claim 1, wherein said different assays comprise Partial Thromboplastin Time, Prothrombin Time, Activated Partial Thromboplastin Time and Factor deficiency assays.

33. The method of claim 1, wherein said first and second predetermined constant times are about two minutes and forty seconds.

34. A method for performing assays to measure hemostasis or thrombosis parameters, comprising:

a) identifying each of a plurality of samples, selecting each sample and scheduling one or more of hemostasis and thrombosis assays to be performed on each sample;

b) providing a plurality of test wells for a plurality of assays and a specimen handler for automatically transferring at a sample insertion station an aliquot of each sample from a holding device to a respective test well of said plurality of test wells;

c) automatically selecting and adding reagents needed for a plurality of different scheduled assays with a sample preparation device to measure hemostasis or thrombosis parameters of the samples in the test wells, wherein in a predetermined first constant time after the sample is delivered to the test well at the sample insertion station, the test well is disposed at a first reagent delivery probe station where a predetermined volume of reagent is optionally added to the test well depending upon the type of assay being performed on the sample in the test well, the volume and temperature of the reagent being variable depending upon which thrombosis or hemostasis assay is being performed;

and wherein in a predetermined second constant time after the test well passes through the first reagent delivery probe station, the test well is disposed at a second reagent delivery probe station where a predetermined volume of a second reagent is optionally added depending upon the type of assay being performed on the sample in the test well, the volume and temperature of the second reagent being variable depending upon which thrombosis or hemostasis assay is being performed;

and wherein in a predetermined third constant time after the test well passes through the second reagent delivery probe station, the test well reaches an optical monitoring station where a reaction of the sample and one or more reagents is monitored by an optical monitoring system for measuring changes in an optical transmission of the sample;

and wherein each of said predetermined constant times remains the same regardless of the hemostasis or thrombosis assay being performed on the sample; and wherein said plurality of test wells for said plurality of assays are moved in the same path relative to said sample preparation means irrespective of the assay being performed on each test well, and wherein a temperature at which said path is maintained and the rate at which the test wells are moved along the path does not vary from assay to assay such that different hemostasis and thrombosis assays can be randomly, continuously and substantially concurrently performed on a fully automated, random access basis;

said monitoring of the reaction of the sample comprising detecting the reaction in each test well and measuring data from each reaction, mathematically processing the measured data to evaluate a change in or magnitude of the measured data from the reaction in the well, and reporting results of the processing of the measured data.

35. The method of claim 34, wherein a plurality of cuvettes are provided, each comprising a plurality of said test wells, and wherein said different assays for measuring thrombosis or hemostasis parameters are performed on one or more samples in different test wells of the same cuvette.

36. The method of claim 34, wherein said different assays comprise Partial Thromboplastin Time, Prothrombin Time, Activated Partial Thromboplastin Time and Factor deficiency assays.

37. The method of claim 34, wherein said first and second predetermined constant times are about two minutes and forty seconds.

38. An instrument for automatically performing assays to measure hemostasis or thrombosis parameters, comprising:

a) a programming input device for identifying each of a plurality of samples and selecting each sample and scheduling one or more of hemostasis and thrombosis assays to be performed on each sample;

b) a plurality of test wells for a plurality of assays and a specimen handler for automatically transferring at a sample insertion station an aliquot of each sample from a holding device to a respective test well of said plurality of test wells;

c) a sample preparation device for automatically selecting and adding reagents needed for a plurality of different scheduled assays to measure hemostasis or thrombosis parameters of the samples in the test wells, a first reagent delivery probe station being provided where a diluent or reagent is optionally added to a test well depending upon the type of assay being performed on the sample in the test well, the test well being disposed at said first reagent delivery probe station in a predetermined first constant time after the sample is delivered to the test well at said sample insertion station, said sample preparation means comprising means for varying at said first reagent delivery probe station the type of reagent and the volume and temperature of the reagent depending upon Which thrombosis or hemostasis assay is being performed;

a second reagent delivery probe station being provided where a reagent is optionally added depending upon the type of assay being performed on the sample in the test well, the test well being disposed at said second reagent delivery probe station in a predetermined second constant time after the test well passes through said first reagent delivery probe station, said sample preparation means comprising a means for varying at said second reagent delivery probe station the type of reagent and the volume and temperature of the reagent depending upon which thrombosis or hemostasis assay is being performed;

an optical monitoring station being provided where a reaction of the sample and one or more reagents is monitored by an optical monitoring system for measuring changes in an optical transmission of the sample, said test well reaching said optical monitoring station in a predetermined third constant time after the test well passes through said second reagent delivery probe station, and wherein each of said predetermined constant times remains the same regardless of the hemostasis or thrombosis assay being performed on the sample, and wherein a temperature at which said path is maintained is constant from assay to assay and the rate at which the test wells are moved along the path by said mover does not vary from assay to assay such that different hemostasis and thrombosis assays can be randomly, continuously and substantially concurrently performed on a fully automated, random access basis;

said optical monitoring system comprising a detector for detecting the reaction in each test well and measuring data from each reaction, a processor for mathematically processing the measured data to evaluate a change in or magnitude of the measured data from the reaction in the well, and reporting results of processing the measured data.

39. The method of claim 1, wherein prior to said test well reaching said optical monitoring system, said test well passes through a third reagent delivery probe station where a reagent is optionally added depending upon the type of assay being performed on the particular sample in the test well, the type of reagent and the volume and temperature of the reagent being variable depending upon which thrombosis or hemostasis assay is being performed.

40. The method of claim 34, wherein prior to said test well reaching said optical monitoring system, said test well passes through a third reagent delivery probe station where a reagent is optionally added depending upon the type of assay being performed on the particular sample in the test well, the type of reagent and the volume and temperature of the reagent being variable depending upon which thrombosis or hemostasis assay is being performed.

* * * * *